United States Patent
Moriya

(10) Patent No.: US 9,109,090 B2
(45) Date of Patent: Aug. 18, 2015

(54) AMINO ACID-MODIFIED ORGANOPOLYSILOXANE, MAKING METHOD, AND COSMETICS

(75) Inventor: Hiroyuki Moriya, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 986 days.

(21) Appl. No.: 13/267,278

(22) Filed: Oct. 6, 2011

(65) Prior Publication Data

US 2012/0093746 A1 Apr. 19, 2012

(30) Foreign Application Priority Data

Oct. 14, 2010 (JP) ................. 2010-231329

(51) Int. Cl.
| | |
|---|---|
| A61K 31/74 | (2006.01) |
| C08G 77/26 | (2006.01) |
| C08G 77/04 | (2006.01) |
| A61K 8/898 | (2006.01) |
| A61Q 5/02 | (2006.01) |
| A61Q 5/12 | (2006.01) |
| C08G 77/388 | (2006.01) |
| C08L 83/08 | (2006.01) |
| A61Q 1/02 | (2006.01) |
| A61Q 1/10 | (2006.01) |
| A61Q 17/04 | (2006.01) |
| A61Q 19/00 | (2006.01) |

(52) U.S. Cl.
CPC ................ *C08G 77/26* (2013.01); *A61K 8/898* (2013.01); *A61Q 5/02* (2013.01); *A61Q 5/12* (2013.01); *C08G 77/04* (2013.01); *C08G 77/388* (2013.01); *C08L 83/08* (2013.01); *A61Q 1/02* (2013.01); *A61Q 1/10* (2013.01); *A61Q 17/04* (2013.01); *A61Q 19/00* (2013.01)

(58) Field of Classification Search
CPC ....................................................... C08G 77/04
See application file for complete search history.

(56) References Cited

U.S. PATENT DOCUMENTS

| | | | |
|---|---|---|---|
| 6,268,454 | B1 | 7/2001 | Song et al. |
| 6,358,501 | B1 | 3/2002 | Dietz et al. |
| 2010/0233104 | A1 | 9/2010 | Drake et al. |

FOREIGN PATENT DOCUMENTS

| | | |
|---|---|---|
| JP | 1-190619 | 7/1989 |
| JP | 3-223207 | 10/1991 |
| JP | 2000-143797 | 5/2000 |
| JP | 2004-182680 | 7/2004 |
| JP | 2009-540040 | 11/2009 |
| WO | WO 2007/141565 A2 | 12/2007 |
| WO | WO 2007/141565 A3 | 12/2007 |

OTHER PUBLICATIONS

Machine translation of JP 2004-182680 A, Jan. 2015.*
Extended Search Report issued Jan. 13, 2012 in Europe Application No. 11184040.1.

* cited by examiner

*Primary Examiner* — Paul Dickinson
(74) *Attorney, Agent, or Firm* — Oblon, McClelland, Maier & Neustadt, L.L.P.

(57) ABSTRACT

An amino acid-modified organopolysiloxane can be prepared under mild reaction conditions by reacting an amino-modified organopolysiloxane with an amino acid or amino acid derivative ester in the presence of an organometallic catalyst. The amino acid-modified organopolysiloxane having a hydrophilic group is useful in cosmetics, powder surface treatment, fiber or fabric treatment, coating, and resin modification.

15 Claims, 3 Drawing Sheets

AMINO ACID-MODIFIED ORGANOPOLYSILOXANE, MAKING METHOD, AND COSMETICS

CROSS-REFERENCE TO RELATED APPLICATION

This non-provisional application claims priority under 35 U.S.C. §119(a) on Patent Application No. 2010-231329 filed in Japan on Oct. 14, 2010, the entire contents of which are hereby incorporated by reference.

TECHNICAL FIELD

This invention relates to an amino acid-modified organopolysiloxane, a method for preparing the same, and a cosmetic composition.

BACKGROUND ART

As to amino acid or peptide-modified silicones and their preparation, a variety of compounds and preparation methods are under investigation. For example, amino acid derivative-modified silicones of the formula shown below are known from JP-A 2004-182680. These amino acid derivative-modified silicones have a structure in which the amino and carboxyl groups of amino acid are protected. While they are prepared using isocyanates or dicyclohexylcarbodiimide, use of such toxic compounds is undesired from the safety aspect. Because of their complex structure, the compounds cannot be prepared in a simple way.

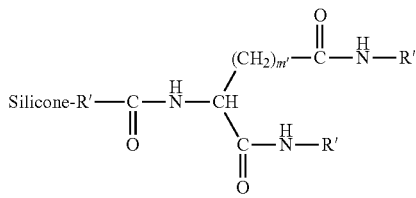

JP-A 2009-540040 discloses that reaction of N-acylamino acid with amino-functional siloxane produces salt and amide compounds. It is described that on thermal reaction, dehydration occurs via a salt compound to form an amide. It is also described that the salt compound is easily obtained, but the dehydration/amidation reaction is slow and it is thus difficult to selectively obtain the amide compound. Namely, the amide compound is obtained while the salt compound is left therein. Due to its nature, the salt compound cannot remain stable at pH levels outside the neutral region. With respect to the amino acids of N-unprotected type having primary, secondary or tertiary amino group, allegedly no effective reaction can be carried out.

In the prior art, amino-modified organopolysiloxanes are known to exert surface protection and softening effects since they adsorb to hair due to the inclusion of amino groups in the molecule (see JP-A H01-190619). In general, hair care cosmetics are kept below pH 5 for preservation or other purposes. Blending the amide compound with some salt left therein in such compositions fails to improve combing and smoothness in hair.

JP-A 2000-143797 discloses that a peptide-silicone copolymer of the formula shown below is obtained utilizing an ability of aspartic acid to form polysuccinimide. The reaction is dangerous because of a high temperature in excess of 160° C. The yield is low since side reactions occur to form unnecessary components, posing a need for extra steps of filtration and washing.

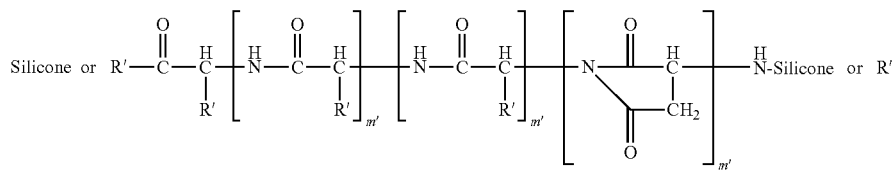

Further, JP-A H03-223207 describes reaction of one end epoxy-modified silicone with an amino group of peptide. This method is undesired since the reactant, epoxy-modified silicone is toxic.

CITATION LIST

Patent Document 1: JP-A 2004-182680
Patent Document 2: JP-A 2009-540040 (WO 2007141565)
Patent Document 3: JP-A H01-190619
Patent Document 4: JP-A 2000-143797
Patent Document 5: JP-A H03-223207

SUMMARY OF INVENTION

An object of the invention is to provide an amino acid-modified organopolysiloxane, a method for preparing an amino acid-modified organopolysiloxane through reaction under mild conditions, and a cosmetic composition comprising amino acid-modified organopolysiloxane, having long lasting performance.

It has been found that an amino acid-modified organopolysiloxane can be prepared under mild reaction conditions by reacting an amino-modified organopolysiloxane with an amino acid or amino acid derivative ester (in the form of an amino acid or amino acid derivative whose carboxyl group has been esterified) in the presence of an organometallic catalyst. It is noted that Patent Document 2 refers nowhere the reaction of amino-functional siloxane with N-acylamino acid ester. Confirming that mere reaction of an amino-modified organopolysiloxane with an amino acid or amino acid derivative ester does not entail amidation, the inventor has found that the reaction must be conducted in the presence of an organometallic catalyst before the ester-amide exchange reaction can proceed.

In a first aspect, the invention provides an amino acid-modified organopolysiloxane having a backbone comprising organosiloxane segments, wherein an organic group having the general formula (1) is bonded to at least one silicon atom in the organosiloxane segments,

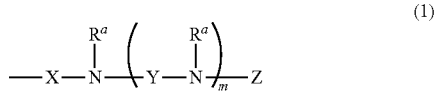
(1)

wherein X and Y are each independently a divalent $C_1$-$C_{10}$ hydrocarbon group, m is an integer of 0 to 4, $R^a$ is hydrogen or a monovalent $C_1$-$C_4$ hydrocarbon group, and Z is an organic group having the general formula (2):

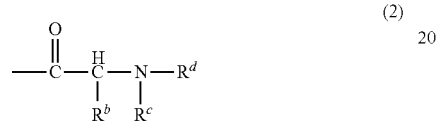
(2)

wherein $R^b$ is a side chain of an amino acid, $R^c$ is hydrogen or $C_1$-$C_6$ alkyl, and $R^d$ is hydrogen, $C_1$-$C_6$ alkyl or $C_1$-$C_{22}$ acyl.

The preferred amino acid-modified organopolysiloxane has the general formula (3):

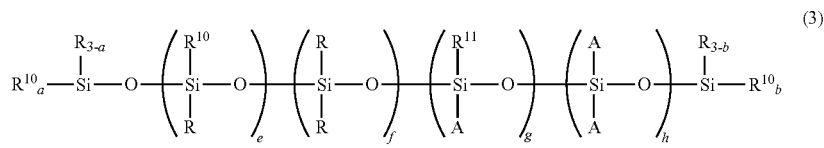
(3)

wherein R is each independently selected from among hydrogen, hydroxyl, $C_1$-$C_3$ alkoxy, $C_1$-$C_{10}$ alkyl, $C_1$-$C_{30}$ fluoroalkyl, $C_6$-$C_{30}$ aryl, and $C_7$-$C_{30}$ aralkyl; $R^{10}$ is an organic group having formula (1); $R^{11}$ is an organic group selected from R and $R^{10}$; A is a segment having the general formula (4):

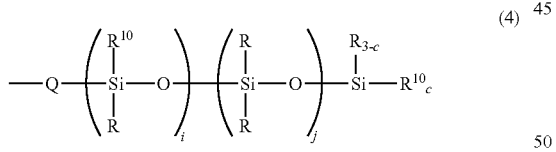
(4)

wherein R and $R^{10}$ are as defined above, and Q is an oxygen atom or a divalent $C_1$-$C_3$ hydrocarbon group; the subscripts a, b, and c are each independently an integer of 0 to 3, e is an integer of 0 to 100, f is an integer of 0 to 5,000, g is 0 or 1, h is 0 or 1, i is an integer of 0 to 100, j is an integer of 0 to 5,000, satisfying $1 \leq a+b+c+e+g+i$ when $R^{11}$ is $R^{10}$, and $1 \leq a+b+c+e+i$ when $R^{11}$ is R.

The amino acid is typically selected from among alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, sarcosine, γ-aminobutyric acid, ornithine, creatine, opine, cystine, hydroxyproline, hydroxylysine, thyroxine, O-phosphoserine, and valine.

In a second aspect, the invention provides a method for preparing an amino acid-modified organopolysiloxane having a backbone comprising organosiloxane segments wherein an organic group having the general formula (1) is bonded to at least one silicon atom in the organosiloxane segments,

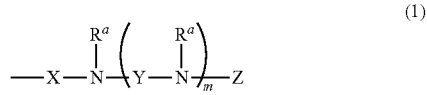
(1)

wherein X and Y are each independently a divalent $C_1$-$C_{10}$ hydrocarbon group, m is an integer of 0 to 4, $R^a$ is hydrogen or a monovalent $C_1$-$C_4$ hydrocarbon group, and Z is an organic group having the general formula (2):

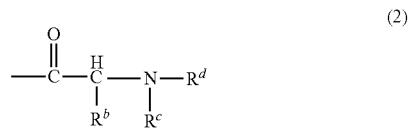
(2)

wherein $R^b$ is a side chain of an amino acid, $R^c$ is hydrogen or $C_1$-$C_6$ alkyl, and $R^d$ is hydrogen, $C_1$-$C_6$ alkyl or $C_1$-$C_{22}$ acyl, said method comprising reacting an amino-modified organopolysiloxane with an amino acid or amino acid derivative ester in the presence of an organometallic catalyst, said amino-modified organopolysiloxane having a backbone comprising organosiloxane segments wherein an amino group having the general formula (5):

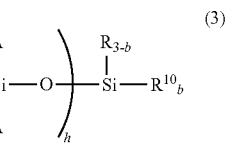
(5)

wherein X, Y, m, and $R^a$ are as defined above is bonded to at least one silicon atom in the organosiloxane segments, said amino acid or amino acid derivative ester being an amino acid or amino acid derivative whose carboxyl group has been esterified and having the general formula (6):

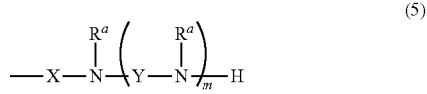
(6)

wherein R' is a monovalent $C_1$-$C_7$ hydrocarbon group, $R^b$, $R^c$, and $R^d$ are as defined above.

In a preferred embodiment, the amino-modified organopolysiloxane has the general formula (7):

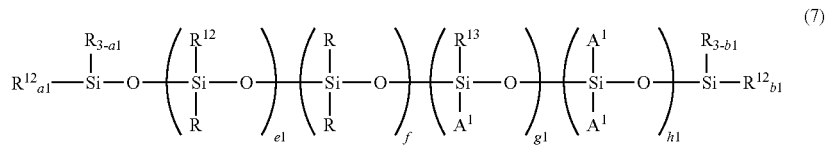
(7)

wherein R is each independently selected from among hydrogen, hydroxyl, $C_1$-$C_3$ alkoxy, $C_1$-$C_{30}$ alkyl, $C_1$-$C_{30}$ fluoroalkyl, $C_6$-$C_{30}$ aryl, and $C_7$-$C_{30}$ aralkyl, $R^{12}$ is an organic group having formula (5), $R^{13}$ is an organic group selected from R and $R^{12}$, $A^1$ is a segment having the general formula (8):

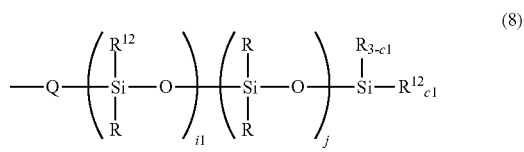
(8)

wherein R and $R^{12}$ are as defined above, and Q is an oxygen atom or a divalent $C_1$-$C_3$ hydrocarbon group, the subscripts a1, b1, and c1 are each independently an integer of 0 to 3, e1 is an integer of 0 to 100, f is an integer of 0 to 5,000, g1 is 0 or 1, h1 is 0 or 1, i1 is an integer of 0 to 100, j is an integer of 0 to 5,000, satisfying $1 \leq a1+b1+c1+e1+g1+i1$ when $R^{11}$ is $R^{12}$, and $1 \leq a1+b1+c1+e1+i1$ when $R^{13}$ is R, and the amino acid-modified organopolysiloxane has the general formula (3):

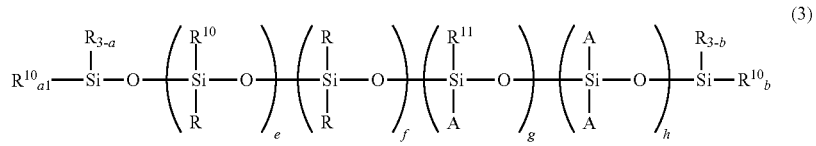
(3)

wherein R is as defined above, $R^{10}$ is an organic group having formula (1), $R^{11}$ is an organic group selected from R and $R^{10}$, A is a segment having the general formula (4):

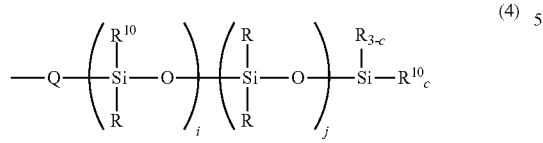
(4)

wherein R, $R^{10}$ and Q are as defined above, a, b, c, e, f, g, h, i, and j are as defined above.

More preferably, the amino acid or amino acid derivative ester has an ester group selected from among methyl, ethyl, propyl, butyl, heptyl, hexyl, and benzyl; the amino acid ester has an amino acid residue which is selected from among alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, sarcosine, γ-aminobutyric acid, ornithine, creatine, opine, cystine, hydroxyproline, hydroxylysine, thyroxine, O-phosphoserine, and valine residues; the amino acid derivative ester has an amino acid derivative residue which is selected from among N-acylamino acid, N-alkylamino acid, and N,N-dialkylamino acid residues. Typically, the N-acyl is acetyl, propanoyl, butanoyl, pentanoyl, hexanoyl, benzoyl, lauroyl, or stearoyl.

In a preferred embodiment, the reaction is conducted in an organic solvent, and the reaction is conducted at a temperature of 25° C. to 120° C.

An organometallic catalyst containing a metal atom selected from the elements of Group 4 and Group 13 in the Periodic Table is effective. The organometallic catalyst is typically a tetraalkoxytitanium, tetraalkoxyzirconium or trialkoxyaluminum.

In a third aspect, the invention provides a cosmetic composition comprising the amino acid-modified organopolysiloxane defined herein, or a cosmetic composition comprising a powder treated with the amino acid-modified organopolysiloxane defined herein.

Advantageous Effects of Invention

The amino acid-modified organopolysiloxane having a hydrophilic group is useful in personal care products or cosmetics, powder surface treatment, fiber or fabric treatment, coating, resin modification, and other applications. The method is successful in preparing the amino acid-modified organopolysiloxane under mild reaction conditions. The cosmetic composition exerts long lasting performance.

DESCRIPTION OF EMBODIMENTS

Figure 1:
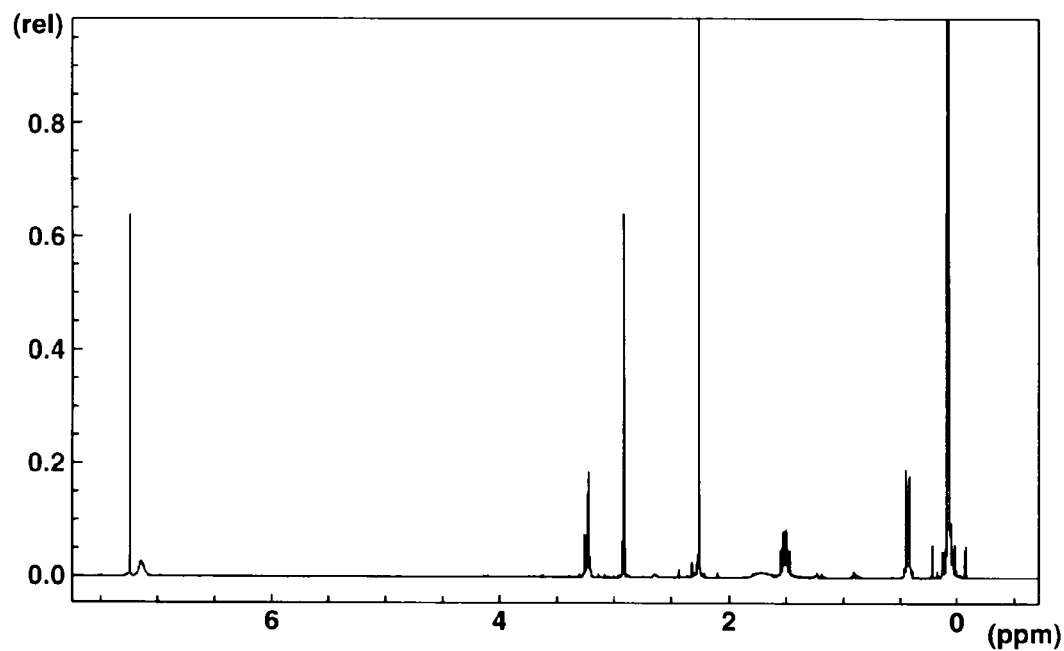
FIGS. 1 and 2 are $^1$H-NMR and IR spectral diagrams of an amino acid-modified organopolysiloxane synthesized in Example 1, respectively.

As used herein, the singular forms "a," "an" and "the" include plural referents unless the context clearly dictates otherwise. The terminology "($C_x$-$C_y$)", as applied to a particular unit, such as, for example, a chemical compound or a chemical substituent group, means having a carbon atom content of from "x" carbon atoms to "y" carbon atoms per such unit.

One embodiment of the invention is an amino acid-modified organopolysiloxane having a backbone comprising organosiloxane segments, wherein an organic group having the general formula (1) is bonded to at least one silicon atom in the organosiloxane segments.

(1)

In formula (1), X and Y are each independently a divalent $C_1$-$C_{10}$ hydrocarbon group, m is an integer of 0 to 4, and $R^a$ is hydrogen or a monovalent $C_1$-$C_4$ hydrocarbon group, typically alkyl. Z is an organic group having the general formula (2):

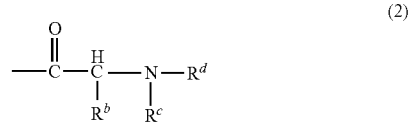
(2)

wherein $R^b$ is a side chain of an amino acid, $R^c$ is hydrogen or $C_1$-$C_6$ alkyl, and $R^d$ is hydrogen, $C_1$-$C_6$ alkyl or $C_1$-$C_{12}$ acyl.

Preferably the amino acid-modified organopolysiloxane is substantially free of a salt of an amino-modified organopolysiloxane with a carboxyl group of an amino acid or amino acid derivative.

Suitable divalent hydrocarbon groups of X and Y include alkylene groups. Suitable acyl groups of $R^d$ include acetyl, propanoyl, butanoyl, pentanoyl, hexanoyl, benzoyl, lauroyl, and stearoyl.

Examples of the amino acid include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, sarcosine, γ-aminobutyric acid, ornithine, creatine, opine, cystine, hydroxyproline, hydroxylysine, thyroxine, O-phosphoserine, and valine.

In a preferred embodiment, the amino acid-modified organopolysiloxane has the general formula (3).

In formula (3), R is each independently selected from among hydrogen, hydroxyl, $C_1$-$C_3$ alkoxy, $C_1$-$C_{30}$ alkyl, $C_1$-$C_{30}$ fluoroalkyl, $C_6$-$C_{30}$ aryl, and $C_7$-$C_{30}$ aralkyl. $R^{10}$ is an organic group having formula (1). $R^{11}$ is an organic group selected from R and $R^{10}$. A is a segment having the general formula (4):

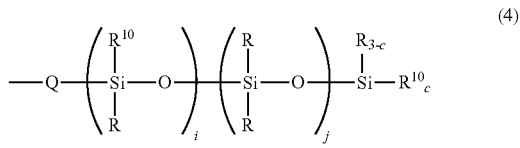
(4)

wherein R and $R^{10}$ are as defined above, and Q is an oxygen atom or a divalent $C_1$-$C_3$ hydrocarbon group, typically alkylene.

In formulae (3) and (4), a, b, and c are each independently an integer of 0 to 3, e is an integer of 0 to 100, f is an integer of 0 to 5,000, g is 0 or 1, h is 0 or 1, i is an integer of 0 to 100, and j is an integer of 0 to 5,000. These subscripts satisfy $1 \le a+b+c+e+g+i$ when $R^{11}$ is $R^{10}$, and $1 \le a+b+c+e+i$ when $R^{11}$ is R.

Examples of $C_1$-$C_{30}$ alkyl groups, $C_1$-$C_{30}$ fluoroalkyl, $C_6$-$C_{30}$ aryl, $C_7$-$C_{30}$ aralkyl, and $C_1$-$C_3$ alkoxy groups represented by R include alkyl groups such as methyl, ethyl, propyl, butyl, pentyl, hexyl, heptyl, octyl, nonyl, decyl, stearyl, cyclopentyl, and cyclohexyl; aryl groups such as phenyl and tolyl; aralkyl groups such as benzyl and phenethyl; fluoroalkyl groups such as trifluoropropyl and heptadecafluorodecyl; and alkoxy groups such as methoxy, ethoxy, and propoxy. Inter alia, $C_1$-$C_{15}$ alkyl groups and phenyl are preferred, with methyl being most preferred. In formulae (3) and (4), a, b, and c are each independently an integer of 0 to 3, e is an integer of 0 to 100, preferably 1 to 50, f is an integer of 0 to 5,000, preferably 1 to 2,000, g is 0 or 1, h is 0 or 1, i is an integer of 0 to 100, preferably 0 to 50, and j is an integer of 0 to 5,000, preferably 0 to 2,000. These subscripts satisfy $15 \le a+b+c+e+g+i$ when $R^{11}$ is $R^{10}$, and $1 \le a+b+c+e+i$ when $R^{11}$ is R.

Another embodiment of the invention is a method for preparing the amino acid-modified organopolysiloxane by reacting (i) an amino-modified organopolysiloxane having a backbone comprising organosiloxane segments wherein an amino group having the general formula (5) is bonded to at least one silicon atom in the organosiloxane segments with (ii) an amino acid or amino acid derivative ester in the form of an amino acid or amino acid derivative whose carboxyl group has been esterified, in the presence of an organometallic catalyst.

Specifically, the desired amino acid-modified organopolysiloxane can be prepared by reacting (i) an amino-modified organopolysiloxane having a backbone comprising organosiloxane segments wherein an amino group having the general formula (5):

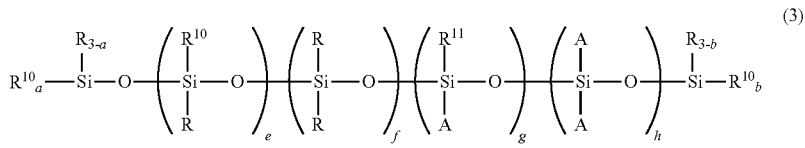
(3)

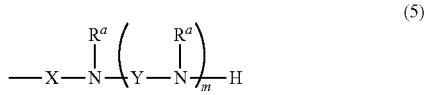

(5)

wherein X and Y are each independently a divalent $C_1$-$C_{10}$ hydrocarbon group, m is an integer of 0 to 4, and $R^a$ is hydrogen or a monovalent $C_1$-$C_4$ hydrocarbon group is bonded to at least one silicon atom in the organosiloxane segments with (ii) an amino acid or amino acid derivative ester in the form of an amino acid or amino acid derivative ester whose carboxyl group has been esterified and having the general formula (6):

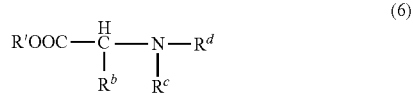

(6)

wherein R' is a monovalent $C_1$-$C_7$ hydrocarbon group, $R^b$ is a side chain of an amino acid, $R^c$ is hydrogen or $C_1$-$C_6$ alkyl, and $R^d$ is hydrogen, $C_1$-$C_6$ alkyl or $C_1$-$C_{22}$ acyl, in the presence of an organometallic catalyst.

The amino-modified organopolysiloxane used herein has a backbone comprising organosiloxane segments wherein the organosiloxane segments are not particularly limited and may be straight, branched or cyclic, preferably straight. Specifically the preferred amino-modified organopolysiloxane has the general formula (7).

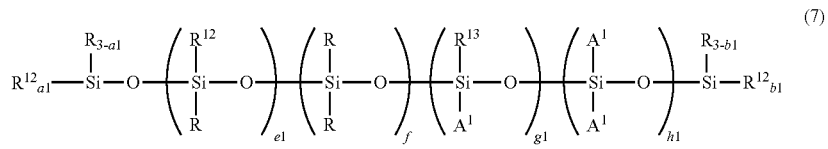

(7)

In formula (7), R has the same meaning as in formula (3), $R^{12}$ is an organic group having formula (5), $R^{13}$ is an organic group selected from R and $R^{12}$, and $A^1$ is a segment having the general formula (8):

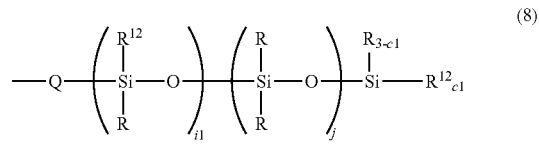

(8)

wherein R, $R^{12}$, and Q are as defined above.

In formulae (7) and (8), a1, b1, and c1 are each independently an integer of 0 to 3, e1 is an integer of 0 to 100, preferably 1 to 50, f is an integer of 0 to 5,000, preferably 1 to 2,000, g1 is 0 or 1, h1 is 0 or 1, i1 is an integer of 0 to 100, preferably 0 to 50, and j is an integer of 0 to 5,000, preferably 0 to 2,000. These subscripts satisfy $1 \le a1+b1+c1+e1+g1+i1$ when $R^{13}$ is $R^{12}$, and $1 \le a1+b1+c1+e1+i1$ when $R^{13}$ is R.

The ester group of the amino acid or amino acid derivative ester is an esterified compound with which a carboxyl group of an amino acid or amino acid derivative is protected. The ester group is preferably selected from among methyl, ethyl, propyl, butyl, heptyl, hexyl, and benzyl, though not limited thereto, with methyl, ethyl and propyl being more preferred.

The amino acid ester used in the preparation of the present organopolysiloxane is commercially available. The precursor amino acid has a structure of the general formula:

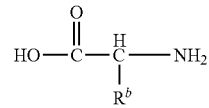

wherein $R^b$ is a side chain of amino acid.

The amino acid ester has an amino acid residue (or moiety) which is selected from common amino acid residues, for example, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, sarcosine, γ-aminobutyric acid, ornithine, creatine, opine, cystine, hydroxyproline, hydroxylysine, thyroxine, O-phosphoserine, and valine residues.

The amino acid derivative ester has an amino acid derivative residue which is typically N-acylamino acid. The N-acylamino acid is an amino acid whose amino group has been protected by amidation. The amino acid moiety is selected from the above-mentioned examples. Examples of the N-acyl group include acetyl, propanoyl, butanoyl, pentanoyl, hexanoyl, benzoyl, lauroyl, and stearoyl, with acetyl, benzoyl, lauroyl and stearoyl being preferred.

The amino acid ester or amino acid derivative ester has the following general formula.

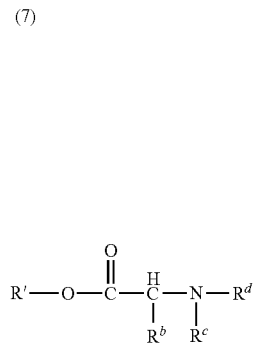

$R^b$ is a side chain of an amino acid. $R^c$ is hydrogen or a $C_1$-$C_6$ alkyl group, preferably hydrogen, methyl, ethyl, or propyl. $R^d$ is selected from hydrogen, $C_1$-$C_6$ alkyl groups, and $C_1$-$C_{22}$ acyl groups such as acetyl, propanoyl, butanoyl, pentanoyl, hexanoyl, benzoyl, lauroyl, and stearoyl, with hydrogen, methyl, ethyl, propyl, acetyl, benzoyl and lauroyl being preferred. The amino group may form a hydrochloride salt. Also included are proline esters in which $R^b$ and $R^d$ connect via alkylene to form a cyclic structure and $R^c$ is hydrogen or methyl, ethyl or propyl. R' is methyl, ethyl, propyl, butyl, pentyl, hexyl, heptyl or benzyl, with methyl, ethyl and propyl being preferred.

The present reaction does not run in the absence of an organometallic catalyst. The organometallic catalyst is typically a Lewis acid metal catalyst. Suitable metals include Group 4 elements such as titanium, zirconium and hafnium, and Group 13 elements such as aluminum, gallium, indium and thallium, which may be used alone or in combination. From the aspects of cost and safety, titanium, zirconium and aluminum are preferred. Examples include titanium tetraalkoxides, zirconium tetraalkoxides, and aluminum trialkoxides, and more specifically, titanium tetraisopropoxide, titanium tetrabutoxide, titanium tetraethoxide, zirconium tetrabutoxide, zirconium tetrabutoxide, zirconium tetraisopropoxide, zirconium tetraethoxide, and aluminum triisopropoxide. An amount of the catalyst used is preferably 0.01 to 1 equivalent, more preferably 0.1 to 0.5 equivalent relative to the amino group of the amino-modified organopolysiloxane, but not limited thereto.

Although the present reaction may take place in a solventless system, an organic solvent may be used. The organic solvent is not particularly limited as long as ester solvents are excluded. Suitable solvents include hydrocarbon solvents such as hexane, heptane, toluene, and xylene, alcohol solvents such as methanol, ethanol, propanol and butanol, ketone solvents such as acetone and methyl ethyl ketone, amide solvents such as N,N-dimethylacetamide, N,N-dimethylformamide, and N-methyl-2-pyrrolidone, ether solvents such as tetrahydrofuran and 1,4-dioxane, and acetonitrile.

Although the reaction temperature is not particularly limited, it is preferably in a range of 25° C. to 120° C., more preferably 60° C. to 100° C. Since the present reaction is a catalytic reaction rather than simple ester-amide exchange reaction, it is not always necessary to carry out the reaction while removing the alcohol component excreted from the ester. Although the reaction time is not particularly limited, it is usually 1 to 15 hours, preferably 1 to 5 hours. Unlike amidation reaction via dehydration, the present amidation reaction is characterized by a low reaction temperature and a high reaction rate.

The present reaction is a reaction of amine with ester, specifically a reaction of the amino-modified organopolysiloxane with the amino acid or amino acid derivative ester. An amount of the ester used is 0.3 to 1.5 equivalents, preferably 0.8 to 1.1 equivalents, and most preferably 1.0 equivalent per equivalent of the amino group of the organopolysiloxane. If it is desired that some amino groups be left behind, the amount of the ester is preferably less than or equal to 1.0 equivalent. The progress of the present reaction may be confirmed by NMR or IR spectroscopy.

Since the preparation of an amino acid-modified organopolysiloxane according to the invention resorts to a reaction of amine with ester, no salt is formed as opposed to the reaction of amine with carboxylic acid entailing salt formation. The amide compound obtained by the present reaction can remain stable in cosmetic compositions, especially aqueous cosmetic compositions, even in ranges outside neutrality (approximately pH 7), especially at or below pH 5. By contrast, a salt of weak acid with weak base like a salt of carboxylic acid with amine is unstable in ranges outside neutrality, especially at or below pH 5.

The present reaction mode may be illustrated by the following reaction schemes, for example. Herein, W denotes siloxane.

The following scheme is an exemplary reaction using N,N-alkylglycine ester.

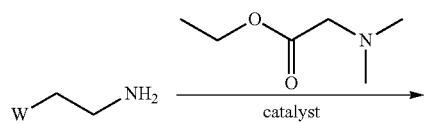

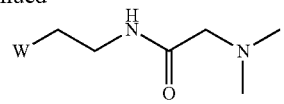

The following scheme is an exemplary reaction using tyrosine ester.

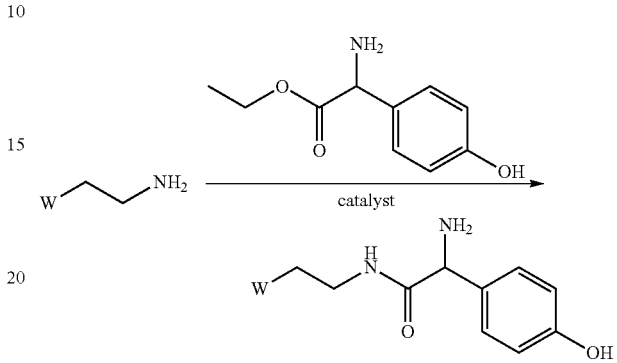

The following scheme is an exemplary reaction using N-acylalanine ester.

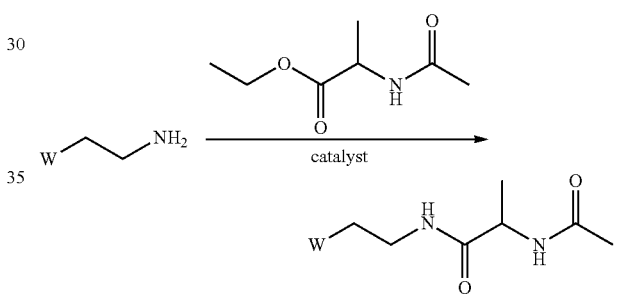

The amino acid-modified organopolysiloxane may find use in various applications, for example, personal care products, cosmetics, powder surface treatment, fiber or fabric treatment, coating, and resin modification.

A further embodiment of the invention is a cosmetic composition comprising the amino acid-modified organopolysiloxane defined herein. In one embodiment, the amino acid-modified organopolysiloxane prepared by the present method may be contained as such. In an alternative embodiment, a powder for cosmetic use may be treated with the amino acid-modified organopolysiloxane and the treated powder may be formulated in the cosmetic composition.

In the alternative embodiment wherein a powder is treated with the amino acid-modified organopolysiloxane, surfaces of particles may be treated by any well-known techniques. A suitable treatment technique may be selected from well-known techniques, for example, surface treatment technique (i) of adding the amino acid-modified organopolysiloxane to a medium such as water or organic solvent, and dispersing powder particles in the medium, and surface treatment technique (ii) of combining powder particles with the amino acid-modified organopolysiloxane and milling the mixture in a ball mill, jet mill or grinder.

In a still further embodiment, a powder treated with the amino acid-modified organopolysiloxane may be dispersed in an oil or fluid. Alternatively, the amino acid-modified organopolysiloxane is dissolved or dispersed in an oil or fluid, a powder is added to the solution or dispersion, and mixing/dispersing operation is carried out. In either case, a liquid dispersion is obtained. The powder-in-oil dispersion may be prepared, for example, by any of well-known techniques including technique (i) of adding the treated powder to an oil or fluid such as ester oil or silicone fluid, followed by dispersion, and technique (ii) of dissolving or dispersing the amino acid-modified organopolysiloxane in an oil or fluid, adding a powder to the solution or dispersion, and milling the mixture in a dispersing machine such as a ball mill, bead mill or sand mill. The particles-in-oil dispersion thus prepared may be directly used and compounded.

When a powder is treated with the amino acid-modified organopolysiloxane having formula (1), the organopolysiloxane may be used in an amount of 0.1 to 30 parts, preferably 0.5 to 10 parts per 100 parts of the powder.

Examples of the powder for cosmetic use include inorganic powders, organic powders, surfactant metal salt powders (metal soaps), colored pigments, pearlescent pigments, metal powder pigments, tar dyes, and natural dyes.

Suitable inorganic powders include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, lithia mica, silicic acid, silicic anhydride, aluminum silicate, magnesium silicate, magnesium aluminum silicate, calcium silicate, barium silicate, strontium silicate, metal tungstates, hydroxyapatite, vermiculite, Higilite®, bentonite, montmorillonite, hectorite, zeolite, ceramic powder, calcium secondary phosphate, alumina, aluminum hydroxide, boron nitride, and silica, all in powder form. In the cosmetic application, body pigments such as mica and sericite, zinc oxide, and titanium oxide are preferable.

Suitable organic powders include polyamide, polyester, polyethylene, polypropylene, polystyrene, polyurethane, benzoguanamine, polymethylbenzoguanamine, tetrafluoroethylene, poly(methyl methacrylate), cellulose, silk, and nylon (e.g., 12-nylon and 6-nylon), all in powder form. Also included are powder forms of styrene-acrylic acid copolymers, divinylbenzene, styrene copolymers, vinyl resins, urea resins, phenolic resins, fluororesins, silicone resins, acrylic resins, melamine resins, epoxy resins, polycarbonate resins, microcrystalline fibrils, starch, and lauroyl lysine.

Suitable surfactant metal salt powders (metal soaps) include zinc stearate, aluminum stearate, calcium stearate, magnesium stearate, zinc myristate, magnesium myristate, zinc cetylphosphate, calcium cetylphosphate, and sodium zinc cetylphosphate.

Suitable colored pigments include powder forms of inorganic red pigments such as iron oxide, iron hydroxide, and iron titanate, inorganic brown pigments such as γ-iron oxide, inorganic yellow pigments such as yellow iron oxide and yellow ocher, inorganic black pigments such as black iron oxide and carbon black, inorganic purple pigments such as manganese violet and cobalt violet, inorganic green pigments such as chromium hydroxide, chromium oxide, cobalt oxide, and cobalt titanate, inorganic blue pigments such as Prussian blue and ultramarine, lake tar dyes, and lake natural dyes, as well as composite powders (combination of the foregoing powders).

Suitable pearlescent pigments include titanium oxide-coated mica, bismuth oxychloride, titanium oxide-coated bismuth oxychloride, titanium oxide-coated talc, fish scales flake, and titanium oxide-coated colored mica. Suitable metal powder pigments include aluminum, copper and stainless steel in powder form.

Suitable tar dyes include Red #3, Red #104, Red #106, Red #201, Red #202, Red #204, Red #205, Red #220, Red #226, Red #227, Red #228, Red #230, Red #401, Red #505, Yellow #4, Yellow #5, Yellow #202, Yellow #203, Yellow #204, Yellow #401, Blue #1, Blue #2, Blue #201, Blue #404, Green #3, Green #201, Green #204, Green #205, Orange #201, Orange #203, Orange #204, Orange #206, and Orange #207. Suitable natural dyes include carminic acid, laccaic acid, carthamin, brazilin, and crocin.

Any of these powders may be used while they are not limited in shape (spherical, needle, plate or the like), particle size (fume, micron or nano-size, pigment grade or the like), and particle structure (porous, nonporous or the like). Also useful are composite powders obtained by combining two or more of the foregoing powders, and the foregoing powders which have been surface treated with oil or fluid, silicones (other than the treating agent of the invention), or fluorinated compounds.

In the cosmetic composition, the amino acid-modified organopolysiloxane is generally compounded in an amount of 0.1 to 50% by weight of the entire composition although the amount may vary with the type and form of the composition.

Suitable ingredients commonly used in conventional cosmetics may be added to the cosmetic composition, for example, solid, semisolid or liquid oil, water, alcohols, water-soluble polymers, film-forming agents, surfactants, oil-soluble gelling agents, organic modified clay minerals, resins, powders, UV absorbers, humectants, preservatives, antiseptic agents, fragrances, salts, antioxidants, pH adjusting agents, chelating agents, refreshing agents, antiinflammatory agents, skin-beautifying agents, vitamins, amino acids, nucleic acids, hormones, and inclusion compounds. Examples of these ingredients are shown below, but the invention is not limited by these ingredients.

Examples of the alcohols used herein include ethanol, propanol, ethylene glycol, ethylene glycol monoalkyl ethers, diethylene glycol monoethyl ether, polyethylene glycol, propylene glycol, dipropylene glycol, 1,3-butylene glycol, glycerol, diglycerol, polyglycerol, pentaerythritol, sucrose, lactose, xylitol, sorbitol, mannitol, maltitol, carrageenan, agar, guar gum, dextrin, tragacanth gum, locust bean gum, polyvinyl alcohol, polyoxyethylene base polymers, polyoxyethylene-polyoxypropylene copolymers, hyaluronic acid, chondroitin sulfate, chitin, and chitosan, which may be used alone or in admixture. The alcohol may be added to the cosmetic composition in a content of 0.1 to 90.0% by weight, preferably 0.5 to 50.0% by weight. A content of less than 0.1 wt % is short for moisture maintenance, antifungal and antibacterial effects whereas a content in excess of 90.0 wt % can prevent the composition from exerting its effect.

Various oily ingredients may be used herein. Examples of natural animal and plant oils and fats and semi-synthetic oils and fats include avocado oil, linseed oil, almond oil, insect wax, perilla oil, olive oil, cacao butter, kapok oil, kaya oil, carnauba wax, liver oil, candelilla wax, beef tallow, beef foot oil, beef bone fat, hardened beef tallow, apricot kernel oil, spermaceti, hardened oil, wheat germ oil, sesame oil, rice germ oil, rice bran oil, sugar cane wax, sasanqua oil, safflower oil, shea butter, Chinese tung oil, cinnamon oil, jojoba wax, shellac wax, turtle oil, soybean oil, tea seed oil, tsubaki oil, tukimiso oil, corn oil, hog fat, rape oil, Japanese tung oil, bran wax, germ oil, horse fat, persic oil, palm oil, palm kernel oil, castor oil, hardened castor oil, castor oil fatty acid methyl ester, sunflower oil, grape oil, bayberry wax, jojoba oil, macadamia nut oil, bees wax, mink oil, cotton seed oil, cotton wax, haze tallow, haze kernel oil, montan wax, coconut oil, hardened coconut oil, tri-coconut oil fatty acid glyceride, mutton tallow, peanut oil, lanolin, liquid lanolin, reduced lanolin, lanolin alcohol, hard lanolin, lanolin acetate, lanolin fatty acid isopropyl, POE lanolin alcohol ether, POE lanolin alcohol acetate, lanolin fatty acid polyethylene glycol, POE hydrogenated lanolin alcohol ether, and egg yolk oil. Note that POE denotes polyoxyethylene.

Examples of hydrocarbon oils include ozokerite, squalane, squalene, ceresin, paraffin, paraffin wax, liquid paraffin, pristane, polyisobutyrene, microcrystalline wax, and vaseline. Exemplary higher fatty acids include lauric acid, myristic acid, palmitic acid, stearic acid, behenic acid, undecylenic acid, oleic acid, linolic acid, linoleic acid, arachidonic acid, eicosapentaenoic acid (EPA), docosahexaenoic acid (DHA), isostearic acid, and 12-hydroxystearic acid.

Exemplary higher alcohols include lauryl alcohol, myristyl alcohol, palmityl alcohol, stearyl alcohol, behenyl alcohol, hexadecyl alcohol, oleyl alcohol, isostearyl alcohol, hexyl dodecanol, octyl dodecanol, setostearyl alcohol, 2-decyl tetradecinol, cholesterol, phytosterol, POE cholesterol ether, monostearyl glycerol ether (batyl alcohol), and monooleyl glycerol ether (cerakyl alcohol).

Exemplary ester oils include diisobutyl adipate, 2-hexyldecyl adipate, di-2-heptylundecyl adipate, N-alkylglycol monoisostearate, isocetyl isostearate, trimethylolpropane triisostearate, ethylene glycol di-2-ethylhexanoate, neopentyl glycol di-2-ethylhexanoate, cetyl 2-ethylhexanoate, trimethylolpropane tri-2-ethylhexanoate, pentaerythritol tetra-2-ethylhexanoate, cetyl octanoate, octyl dedecyl gum ester, oleyl oleate, octyl dodecyl oleate, decyl oleate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxylstearate, dipentaerythritol fatty acid ester, isopropyl myristate, 2-octyldodecyl myristate, 2-hexyldecyl myristate, myristyl myristate, hexyldecyl dimethyloctanoate, ethyl laurate, hexyl laurate, N-lauroyl-L-glutamic acid-2-octyldodecyl ester, diisostearyl malate, dextrin palmitic acid ester, dextrin stearic acid ester, dextrin 2-ethylhexanoic acid palmitic acid ester, sucrose palmitic acid ester, sucrose stearic acid ester, monobenzylidene sorbitol, and dibenzylidene sorbitol.

Exemplary glyceride oils include acetoglyceride, glyceryl diisooctanoate, glyceryl triisostearate, glyceryl triisopalmitate, glyceryl tri-2-ethylhexanoate, glyceryl monostearate, glyceryl di-2-heptylundecanoate, and glyceryl trimyristate.

Exemplary silicone oils include higher alkoxy-modified silicones and higher fatty acid-modified silicones such as dimethylpolysiloxane, methylphenylpolysiloxane, methylhydrogenpolysiloxane, octamethylcyclotetrasiloxane, decamethylcyclopentasiloxane, dodecamethylcyclohexasiloxane, tetramethyltetrahydrogencyclotetrasiloxane, and stearoxysilicone as well as fluorine-modified silicones, amino-modified silicones, alkyl-modified silicones, higher fatty acid ester-modified silicones, silicone resins, and silicone rubbers. Exemplary fluorochemical oils include perfluoropolyether, perfluorodecalin, and perfluorooctane.

These oily ingredients may be used alone or in admixture of two or more. The oil may be added to the cosmetic composition in a content of 0 to 90.0% by weight, preferably 1 to 90% by weight. When water is added to the cosmetic composition, the water content ranges from 0 to 99.0% by weight.

The cosmetic composition may be prepared by combining the foregoing ingredients. Optionally, any of additional ingredients i), ii), iii) and iv) as shown below may be further blended.

i) Powder and/or Colorant

Exemplary inorganic powders include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, lithia mica, silicic acid, silicic anhydride, aluminum silicate, magnesium silicate, aluminum magnesium silicate, calcium silicate, barium silicate, strontium silicate, metal salts of tungstenic acid, hydroxyapatite, vermiculite, Higilite®, bentonite, montmorillonite, hectorite, zeolite, ceramic powder, calcium secondary phosphate, alumina, aluminum hydroxide, boron nitride, and silica.

Exemplary organic powders include polyamide powder, polyester powder, polyethylene powder, polypropylene powder, polystyrene powder, polyurethane, benzoguanamine powder, polymethylbenzoguanamine powder, tetrafluoroethylene powder, polymethyl methacrylate powder, cellulose, silk powder, nylon powder, 12-nylon, 6-nylon, styrene-acrylic acid copolymers, divinyl benzene-styrene copolymers, vinyl resins, urea resins, phenolic resins, fluoro-resins, silicon resins, acrylic resins, melamine resins, epoxy resins, polycarbonate resins, microcrystalline fiber powder, rice starch, and lauroyl lysine.

Suitable surfactant metal salt powders or metal soaps include zinc stearate, aluminum stearate, calcium stearate, magnesium stearate, zinc myristate, magnesium myristate, zinc cetyl phosphate, calcium cetyl phosphate, and zinc sodium cetyl phosphate.

Suitable color pigments include inorganic red pigments such as iron oxide, iron hydroxide, and iron titanate; inorganic brown pigments such as γ-iron oxide; inorganic yellow pigments such as yellow iron oxide and ochre; inorganic black pigments such as black iron oxide and carbon black; inorganic purple pigments such as manganese violet and cobalt violet; inorganic green pigments such as chromium hydroxide, chromium oxide, cobalt oxide, and cobalt titanate; inorganic blue pigments such as Prussian blue and ultramarine; lake-form tar dyes, lake-form natural dyes, as well as composite powders obtained by combining the foregoing powders.

Suitable pearlescent pigments include titanium oxide-coated mica, bismuth oxychloride, titanium oxide-coated bismuth oxychloride, titanium oxide-coated talc, fish scale flake, and titanium oxide-coated color mica. Suitable metal powder pigments include aluminum powder, copper powder and stainless steel powder.

Suitable tar dyes include Red #3, Red #104, Red #106, Red #201, Red #202, Red #204, Red #205, Red #220, Red #226, Red #227, Red #228, Red #230, Red #401, Red #505, Yellow #4, Yellow #5, Yellow #202, Yellow #203, Yellow #204, Yellow #401, Blue #1, Blue #2, Blue #201, Blue #404, Green #3, Green #201, Green #204, Green #205, Orange #201, Orange #203, Orange #204, Orange #206 and Orange #207. Suitable natural dyes include carminic acid, laccaic acid, carthamin, brazilin and crocin.

Any of these powders which are used in conventional cosmetic compositions may be used without restriction on its shape (inclusive of spherical, needle and plate shapes), particle size (inclusive of fume, micro or nano-size, and pigment grade), and particle structure (inclusive of porous and nonporous). Further, these powders may be combined into composite powders or surface treated with ordinary oil ingredients, silicones other than formula (1), fluorine compounds or the like.

ii) Surfactant

Illustrative examples of anionic surfactants include saturated or unsaturated fatty acid soaps such as sodium stearate and triethanol amine oleate, carboxylic acid salts such as alkyl ether carboxylic acids and salts thereof, and condensates of amino acid and fatty acid, and amide ether carboxylic acid salts, α-sulfofatty acid ester salts, α-acylsulfonic acid salts, alkylsulfonic acid salts, alkenesulfonic acid salts, sulfonic acid salts of fatty acid esters, sulfonic acid salts of fatty acid amides, sulfonic acid salts such as alkylsulfonic acid salts and formalin condensates, alkyl sulfuric acid ester salts, secondary higher alcohol sulfuric acid ester salts, alkyl and allyl ether sulfuric acid ester salts, sulfuric acid ester salts of fatty acid esters, sulfuric acid ester salts of fatty acid alkylolamide, sulfuric acid ester salts such as sulfonated oil, alkyl phosphates, alkenyl phosphates, ether phosphates, alkyl allyl ether phosphates, alkyl amide phosphates, and N-acylamino acid base surfactants.

Illustrative examples of cationic surfactants include amine salts such as alkyl amine salts, polyamine and aminoalcohol fatty acid derivatives; alkyl quaternary ammonium salts, aromatic quaternary ammonium salts, pyridinium salts, and imidazolium salts.

Illustrative examples of nonionic surfactants include sorbitol fatty acid esters, glycerol fatty acid esters, polyglycerol fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene alkyl phenyl ethers, polyoxyethylene fatty acid esters, polyoxyethylene sorbitol fatty acid esters, polyoxyethylene sorbitan fatty acid esters, polyoxyethylene glycerol fatty acid esters, polyoxyethylene propylene glycol fatty acid esters, polyoxyethylene castor oil, polyoxyethylene hardened castor oil, polyoxyethylene phytostanol ether, polyoxyethylene phytosterol ether, polyoxyethylene cholestanol ether, polyoxyethylene cholesteryl ether, polyoxyalkylene-modified organopolysiloxane, polyoxyalkylene/alkyl-co-modified organopolysiloxane, polyoxyalkylene/fluoroalkyl-co-modified organopolysiloxane, polyoxyalkylene/organopolysiloxane block copolymers, alkanol amides, saccharide ethers, and saccharide amides. Illustrative examples of ampholytic surfactants include betaine, aminocarboxylic acid salts, and imidazoline derivatives.

iii) Crosslinked Organopolysiloxanes

In the cosmetic composition, one or more crosslinked organopolysiloxanes may be used. The crosslinked organopolysiloxane is preferably a silicone having a low viscosity of 0.65 to 10.0 mm$^2$/sec at 25° C. which will swell by containing a low viscosity silicone in an amount of more than its own weight. The crosslinked organopolysiloxane preferably has a crosslinked structure obtained by reaction of a crosslinker having at least two vinyl reactive sites in the molecule with a silicon-bonded hydrogen atom. The crosslinked organopolysiloxane preferably contains a moiety of at least one type selected from among polyoxyalkylene, alkyl, alkenyl, aryl, and fluoroalkyl moieties. When used, the crosslinked organopolysiloxane is preferably blended in an amount of 0.1 to 30% by weight, more preferably 1 to 10% by weight of the total weight of the cosmetic composition.

iv) Silicone Resins Such as Acrylic/Silicone Graft or Block Copolymers And Silicone Network Compounds In the cosmetic composition, one or more silicone resins such as acrylic/silicone graft or block copolymers and silicone network compounds may be used. The preferred silicone resins are acrylic/silicone resins, more preferably acrylic/silicone resins containing in the molecule at least one moiety selected from among pyrrolidone, long-chain alkyl, polyoxyalkylene, and fluoroalkyl moieties. Silicone network compounds are also preferred as the silicone resin. When used, the silicone resin is preferably blended in an amount of 0.1 to 20% by weight, more preferably 1 to 10% by weight of the total weight of the cosmetic composition.

The cosmetic composition finds use in various applications, preferably makeup preparations and UV screen preparations. These preparations may take any desired forms including liquid, emulsion, cream, solid, paste, gel, powder, multilayer, moose, and aerosol (spray).

Among various types of cosmetic compositions, hair care products are preferred. In the hair care product, the amino acid-modified organopolysiloxane is preferably contained in an amount of 0.1 to 20%, more preferably 1 to 10%, and even more preferably 1 to 5% by weight to achieve better conditioning effect and long-lasting performance thereof.

The hair care product may further contain an oily ingredient, specifically an oily ingredient having conditioning effect on hair. Suitable oily ingredients include lower alcohols and saturated or unsaturated alcohols of 12 to 30 carbon atoms; ethers of the foregoing alcohols and polyhydric alcohols; esters of the foregoing alcohols with fatty acids of 1 to 11 carbon atoms; saturated or unsaturated fatty acids of 12 to 30 carbon atoms; esters of the foregoing fatty acids with mono- or dihydric alcohols; amides of the foregoing fatty acids with amines; sterol; squalene; phosphatide; glycolipid; animal fats and oils; plant fats and oils; and one or more of cyclic, straight or branched dimethylpolysiloxane, methylpolysiloxane, polysiloxane, alkyl-modified silicone, methylphenylpolysiloxane, and polyether-modified silicone. The oily ingredient is preferably contained in an amount of 0.01 to 30% by weight, more preferably 1 to 25% by weight, and even more preferably 3 to 20% by weight of the hair care product.

The hair care product may further contain other ingredients insofar as the desired effects are not impaired. Suitable ingredients include thickeners such as hydroxyethyl cellulose, surfactants, anionic, ampholytic, cationic and nonionic polymers, fragrances, pearlescent agents, hair setting polymers, dyes, UV absorbers, antioxidants, and preservatives.

The surfactant used herein is not particularly limited and selected from well-known surfactants which are used in conventional hair care products. The surfactants used herein may be anionic, cationic, nonionic or ampholytic.

Illustrative examples of anionic surfactants include alkylbenzene sulfonic acid salts, preferably alkylbenzene sulfonic acid salts having a straight or branched alkyl group of 10 to 16 carbon atoms on average; alkyl ether sulfuric acid salts or alkenyl ether sulfuric acid salts, preferably alkyl ether sulfuric acid salts or alkenyl ether sulfuric acid salts having a straight or branched alkyl or alkenyl group of 10 to 20 carbon atoms on average and having added thereto, on average per molecule, 0.5 to 8 moles of ethylene oxide, propylene oxide, butylene oxide, ethylene oxide and propylene oxide in a molar ratio of 0.1/9.9 to 9.9/0.1, or ethylene oxide and butylene oxide in a molar ratio of 0.1/9.9 to 9.9/0.1; alkyl sulfuric acid salts or alkenyl sulfuric acid salts, preferably alkyl sulfuric acid salts or alkenyl sulfuric acid salts having an alkyl or alkenyl group of 10 to 20 carbon atoms on average; olefin sulfonic acid salts, preferably olefin sulfonic acid salts having 10 to 20 carbon atoms on average per molecule; alkane sulfonic acid salts, preferably alkane sulfonic acid salts having 10 to 20 carbon atoms on average per molecule; higher fatty acid salts, preferably saturated or unsaturated fatty acid salts having 10 to 24 carbon atoms on average per molecule;

(amide) ether carboxylic acid surfactants; α-sulfofatty acid salts or esters, preferably α-sulfofatty acid salts or esters having an alkyl or alkenyl group of 10 to 20 carbon atoms on average; N-acylamino acid surfactants, preferably N-acylamino acid surfactants having an acyl group of 8 to 24 carbon atoms and a free carboxylic acid residue (e.g., N-acylsarcosinate, N-acyl-β-alanine); phosphoric acid ester surfactants, preferably phosphoric acid mono- or diester surfactants having an alkyl or alkenyl group of 8 to 24 carbon atoms or an alkylene oxide adduct thereof; sulfosuccinic acid ester surfactants, preferably sulfosuccinic acid esters of higher alcohols of 8 to 22 carbon atoms or ethoxylate thereof or sulfosuccinic acid esters derived from higher fatty acid amides; polyoxyalkylene fatty acid amide ether sulfuric acid salts, preferably sulfuric acid salts of ethoxylates of straight or branched, saturated or unsaturated fatty acid monoethanol amide or diethanol amide of 8 to 24 carbon atoms; monoglyceride sulfuric acid ester salts, preferably monoglyceride sulfuric acid ester salts having a straight or branched, saturated or unsaturated fatty acid group of 8 to 24 carbon atoms; acylated isethionic acid salts, preferably acylated isethionic acid salts having a straight or branched, saturated or unsaturated fatty acid group of 8 to 24 carbon atoms; alkylglyceryl ether sulfuric acid salts or alkylglyceryl ether sulfonic acid salts, preferably alkylglyceryl ether sulfuric acid salts or alkylglyceryl ether sulfonic acid salts having a straight or branched alkyl or alkenyl group of 8 to 24 carbon atoms or an alkylene oxide adduct thereof; alkyl or alkenyl amide sulfonates, preferably alkyl or alkenyl amide sulfonates having a straight or branched alkyl or alkenyl group of 8 to 24 carbon atoms; alkanol amide sulfosuccinic acid salts, preferably alkanol amide sulfosuccinic acid salts having a straight or branched alkyl or alkenyl group of 8 to 24 carbon atoms; alkyl sulfoacetates, preferably alkyl sulfoacetates having a straight or branched alkyl or alkenyl group of 8 to 24 carbon atoms; acylated taulates, preferably acylated taulates having a straight or branched, saturated or unsaturated fatty acid group of 8 to 24 carbon atoms; N-acyl-N-carboxyethyl glycine salts, preferably N-acyl-N-carboxyethyl glycine salts having an acyl group of 6 to 24 carbon atoms.

In the salts of these anionic surfactants, examples of the counter ion to the anionic residue include alkali metal ions such as sodium and potassium, alkaline earth metal ions such as calcium and magnesium, ammonium ion, and alkanolamines having one, two or three alkanol groups of 2 or 3 carbon atoms (e.g. monoethanol amine, diethanol amine, triethanol amine, triisopropanol amine). Of the foregoing anionic surfactants, preference is given to the alkyl ether sulfuric acid salts, especially polyoxyethylene alkyl ether sulfuric acid salts.

Illustrative examples of nonionic surfactants include polyoxyalkylene alkyl ethers or polyoxyalkylene alkenyl ethers having a straight or branched alkyl or alkenyl group of 10 to 24 carbon atoms on average and having added thereto ethylene oxide, propylene oxide or butylene oxide; glycerol esters of fatty acids of 8 to 20 carbon atoms; glycol esters of fatty acids of 8 to 20 carbon atoms; alkylene oxide adducts of $C_8$-$C_{20}$ fatty acid monoglycerides; sucrose esters of fatty acids of 8 to 20 carbon atoms; sorbitan esters of fatty acids of 8 to 20 carbon atoms; polyglycerol fatty acid esters having an acyl group of 8 to 20 carbon atoms; monoethanol amides or diethanol amides of fatty acids of 8 to 20 carbon atoms or ethoxylates thereof; polyoxyethylene-hardened castor oil; polyoxyalkylene sorbitan fatty acid esters having an acyl group of 8 to 20 carbon atoms; polyoxyethylene sorbitol fatty acid esters having an acyl group of 8 to 20 carbon atoms; alkyl saccharide surfactants having a straight or branched alkyl, alkenyl or alkylphenyl group of 8 to 18 carbon atoms; alkylamine oxide or alkylamidoamine oxide having a straight or branched alkyl or alkenyl group of 8 to 20 carbon atoms; ether or ester compounds of polyhydric alcohols having a straight or branched alkyl or alkenyl group of 8 to 20 carbon atoms; polyoxyalkylene-modified organopolysiloxanes, polyoxyalkylene/alkyl-co-modified organopolysiloxanes, polyglycerol-modified organopolysiloxanes, polyglycerol/alkyl-co-modified organopolysiloxanes, polyoxyalkylene/fluoroalkyl-co-modified organopolysiloxanes, crosslinked polyoxyalkylene-organopolysiloxanes, sucrose-modified silicones, oxazoline-modified silicones, polyoxyalkylene alkyl aryl ether, polyoxyalkylene lanoline alcohols, polyoxyalkylene fatty acid esters, Pluronic block polymers, Tetronic block polymers, polyoxyalkylene fatty acid amides, polyoxyalkylene alkyl amides, and polyethylene imine derivatives.

Suitable ampholytic surfactants used herein include those commonly used in conventional hair care products, for example, amidoamino acid, carbobetaine, amidobetaine, sulfobetaine, amidosulfobetaine, imidazolinium betaine, amino acid, phosphobetaine, and phosphate based surfactants.

Suitable cationic surfactants include tertiary amines, quaternary ammonium salts, amidoamines, and ester amines. Examples include behenyltrimethylammonium chloride, distearyldimethylammonium chloride, cetyltrimethylammonium chloride, stearyltrimethylammonium chloride, laurylt-rimethylammonium chloride, N-stearyl-N,N,N-tri(polyoxyethylene)ammonium chloride (having 3 moles of ethylene oxide added in total), cetylbenzyldimethylammonium chloride, cetyltriethylammonium bromide, and distearyldimethylammonium chloride, as well as 2-decyltetradecyltrimethylammonium chloride, 2-dedecylhexadecyltrimethylammonium chloride, di-2-hexyldecyldimethylammonium chloride, di-2-octyldodecyldimethylammonium chloride, behenyl tertiary amines, stearyl tertiary amines, and stearamidopropyldimethylamine.

One or more surfactants may be used. Preferably the surfactant is used in an amount of 0.1 to 50% by weight in the hair care product. For foamability, the amount of the surfactant is more preferably 0.5 to 40%, and even more preferably 1 to 30% by weight.

When the hair care product takes a hair setting, hair foam or hair spray form, suitable polymers may be contained for hair setting purpose. Examples of hair setting polymers include polyvinylpyrrolidone, vinylpyrrolidone/vinyl acetate copolymers, vinylpyrrolidone/vinyl acetate/vinyl propionate crosslinked copolymers, vinylpyrrolidone/alkylaminoacrylate copolymers, vinylpyrrolidone/acrylate/(meth)acrylic acid copolymers, vinylpyrrolidone/alkylaminoacrylate/vinyl caprolactam copolymers; methyl vinyl ether/maleic anhydride alkyl half-ester copolymers; vinyl acetate/crotonic acid copolymers, vinyl acetate/crotonic acid/vinyl neodecanoate copolymers, vinyl acetate/crotonic acid/vinyl propionate copolymers, and vinyl acetate/vinyl tert-butylbenzoate/-crotonic acid copolymers; (meth)acrylic acid/(meth)acrylate copolymers, and acrylic acid/alkyl acrylate/alkyl acrylamide copolymers; (meth)acrylethylbetaine/alkyl (meth)acrylate copolymers, N-methacryloyloxyethyl-N,N-dimethylammonium α-N-methylcarboxybetaine/alkyl (meth)acrylate copolymers, alkyl acrylate/butylaminoethyl methacrylate/acrylic acid octylamide copolymers; basic acrylic polymers; compounds of cellulose structure, cationic cellulose derivatives; hydroxypropyl chitosan, carboxymethyl chitin, carboxymethyl chitosan, and salts of chitosan with a monobasic acid such as pyrrolidone carboxylic acid, lactic acid or glycolic acid or a dibasic acid such as adipic acid or succinic acid; and water-dispersible polyesters.

One or more hair setting polymers may be used. The hair setting polymer is used in an amount to provide a necessary and sufficient setting force, preferably 0.1 to 10%, more preferably 0.5 to 6%, and even more preferably 1 to 4% by weight of the hair care product.

Examples of the hair care product include hair shampoo, hair treatment, and hair conditioner as typically used in the bath room, hair foam, hair spray, hair cream, hair wax, and hair gel, as typically used outside the bath room, hair dye, permanent wave agent, hair manicure, and hair bleach for household and beauty salon use. The present amino acid-modified organopolysiloxane may be blended in any of these products.

EXAMPLE

Examples of the invention are given below by way of illustration and not by way of limitation. All parts and % are by weight. The viscosity is measured at 25° C. by an Ostwald viscometer.

Example 1

Figure 2:
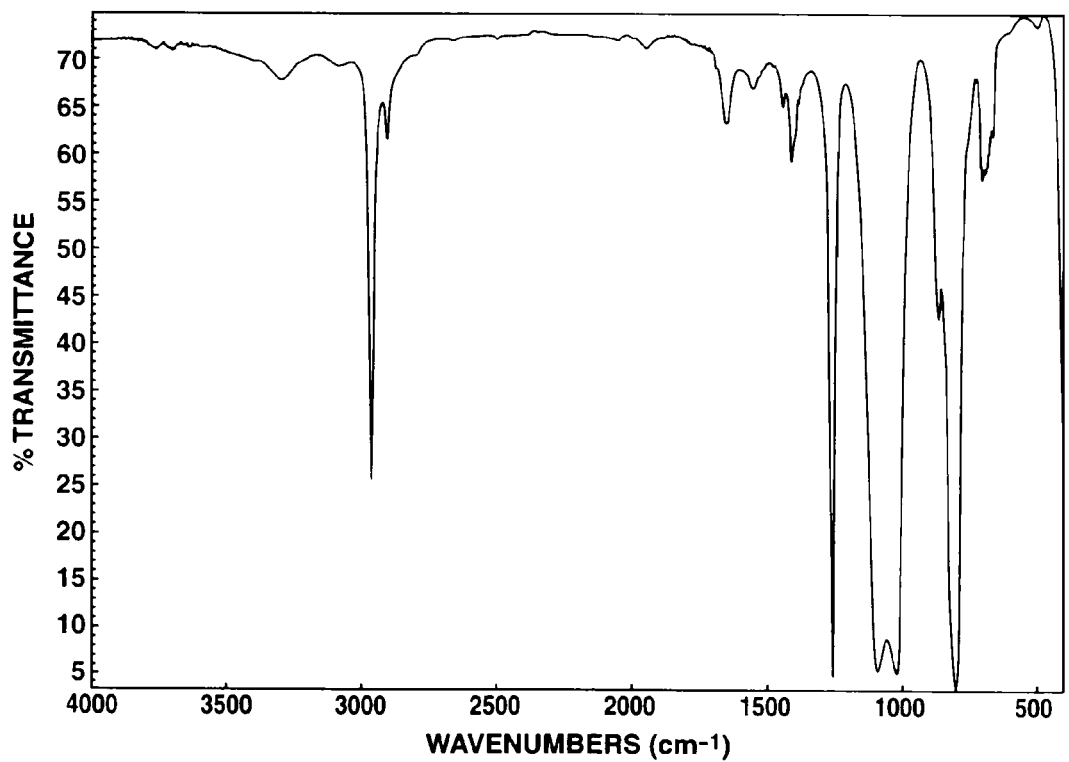

A reactor was charged with 80 parts of tris(trimethylsiloxy) silylpropylamine, 5 parts of titanium tetraisopropoxide, and 30 parts of N,N-dimethylglycine ethyl. The contents were stirred at 80° C. for 4 hours. The reaction mixture was stripped at 100° C. in vacuum, obtaining 105 parts of a pale yellow liquid in a yield of 96%. FIG. 1 shows the measurement results of $^1$H-NMR spectroscopy. The peak at 2.6 ppm assigned to the amine reactant extinguished and instead, the peak at approximately 3.1 ppm assigned to the amide bond formed was observed. FIG. 2 shows the measurement results of IR spectroscopy. The absorption peak at 1,680 cm$^{-1}$ assigned to amide bond was observed, confirming that N,N-dimethylglycine ethyl was bound to tris(trimethylsiloxy)silylpropylamine.

Example 2

Figure 3:
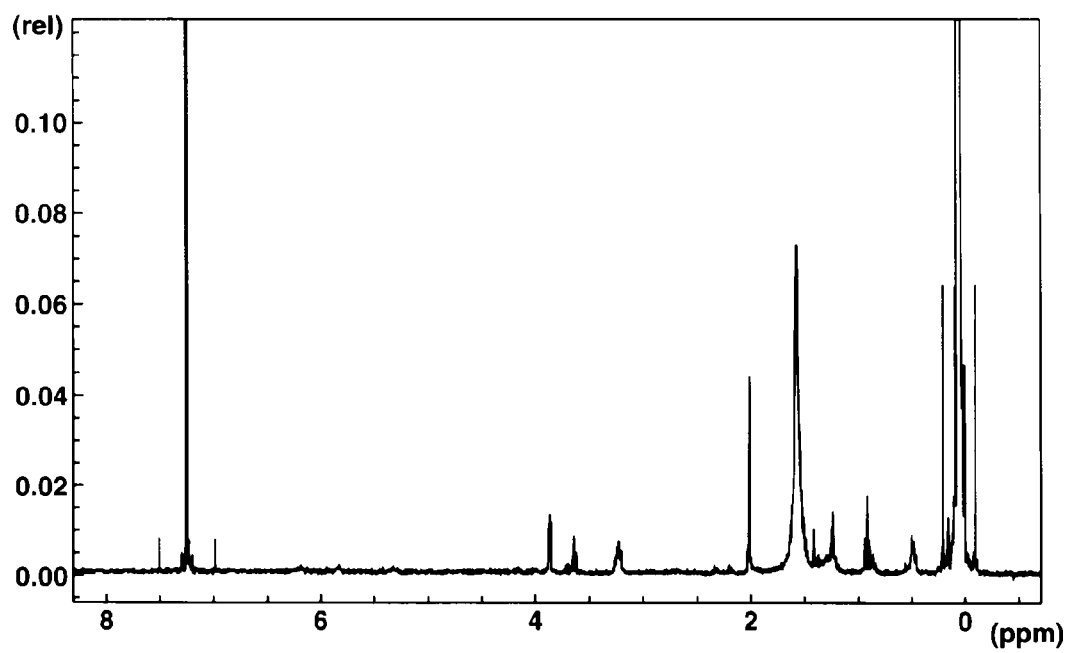
FIGS. 3 and 4 are $^1$H-NMR and IR spectral diagrams of an amino acid-modified organopolysiloxane synthesized in Example 2, respectively.
Figure 4:
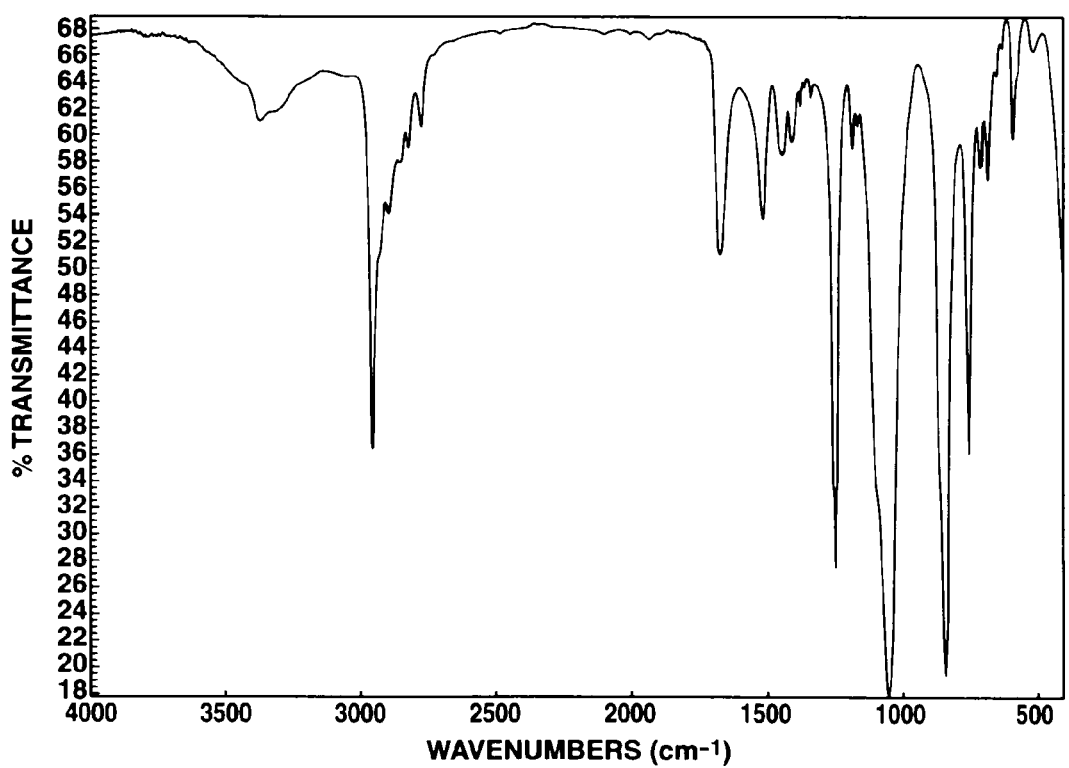

A reactor was charged with 450 parts of a side chain aminopropylmethylsiloxane/dimethylsiloxane copolymer having an amine equivalent of 4,800 g/mol and a viscosity of 110 mm$^2$/sec at 25° C., 4 parts of titanium tetrabutoxide, and 14 parts of N-acetylglycine ethyl. The contents were stirred at 100° C. for 8 hours. The reaction mixture was stripped at 120° C. in vacuum, obtaining 430 parts of a pale yellow, faintly turbid liquid in a yield of 93%. FIG. 3 shows the measurement results of $^1$H-NMR spectroscopy. The peak at 2.6 ppm assigned to the amine reactant extinguished and instead, the peak at approximately 3.1 ppm assigned to the amide bond formed was observed. FIG. 4 shows the measurement results of IR spectroscopy. The absorption peak at 1,650 cm$^{-1}$ assigned to amide bond was observed, confirming that N,N-dimethylglycine ethyl was bound to the aminopropyl-containing polysiloxane.

Example 3

A reactor was charged with 300 parts of a side chain aminopropylmethylsiloxane/dimethylsiloxane copolymer having an amine equivalent of 6,800 g/mol and a viscosity of 1,800 mm$^2$/sec at 25° C., 8 parts of aluminum triisopropoxide, and 9 parts of N-benzoylglycine ethyl. The contents were stirred at 100° C. for 10 hours. The reaction mixture was stripped at 120° C. in vacuum, obtaining 290 parts of a pale yellow, faintly turbid, viscous liquid in a yield of 95%. In the $^1$H-NMR spectrum, the peak at 2.6 ppm assigned to the amine reactant extinguished and instead, the peak at approximately 3.1 ppm assigned to the amide bond formed was observed. In the IR spectrum, the absorption peak at 1,650 cm$^{-1}$ assigned to amide bond was observed, confirming that N,N-benzoylglycine ethyl was bound to the aminopropyl-containing polysiloxane.

Example 4

A reactor was charged with 500 parts of a both end aminopropylsiloxy-terminated polysiloxane having an amine equivalent of 1,480 g/mol and a viscosity of 60 mm$^2$/sec at 25° C., 50 parts of toluene, 11 parts of titanium tetrabutoxide, and 65 parts of tyrosine ethyl. The contents were stirred at 100° C. for 8 hours. The reaction mixture was stripped at 120° C. in vacuum, obtaining 536 parts of a pale yellow, faintly turbid, viscous liquid in a yield of 95%. In the $^1$H-NMR spectrum, the peak at 2.6 ppm assigned to the amine reactant extinguished and instead, the peak at approximately 3.1 ppm assigned to the amide bond formed was observed. In the IR spectrum, the absorption peak at 1,650 cm$^{-1}$ assigned to amide bond was observed, confirming that tyrosine ethyl was bound to the aminopropyl-containing polysiloxane.

Example 5

A reactor was charged with 600 parts of a side chain aminopropylmethylsiloxane/dimethylsiloxane copolymer having an amine equivalent of 3,610 g/mol and a viscosity of 1,800 mm$^2$/sec at 25° C., 22 parts of titanium tetraethoxide, and 28 parts of 1-ethylproline ethyl. The contents were stirred at 100° C. for 8 hours. The reaction mixture was stripped at 120° C. in vacuum, obtaining 596 parts of a pale yellow, faintly turbid, viscous liquid in a yield of 95%. In the $^1$H-NMR spectrum, the peak at 2.6 ppm assigned to the amine reactant extinguished and instead, the peak at approximately 3.1 ppm assigned to the amide bond formed was observed. In the IR spectrum, the absorption peak at 1,660 cm$^{-1}$ assigned to amide bond was observed, confirming that 1-ethylproline ethyl was bound to the aminopropyl-containing polysiloxane.

Example 6

Figure 5:
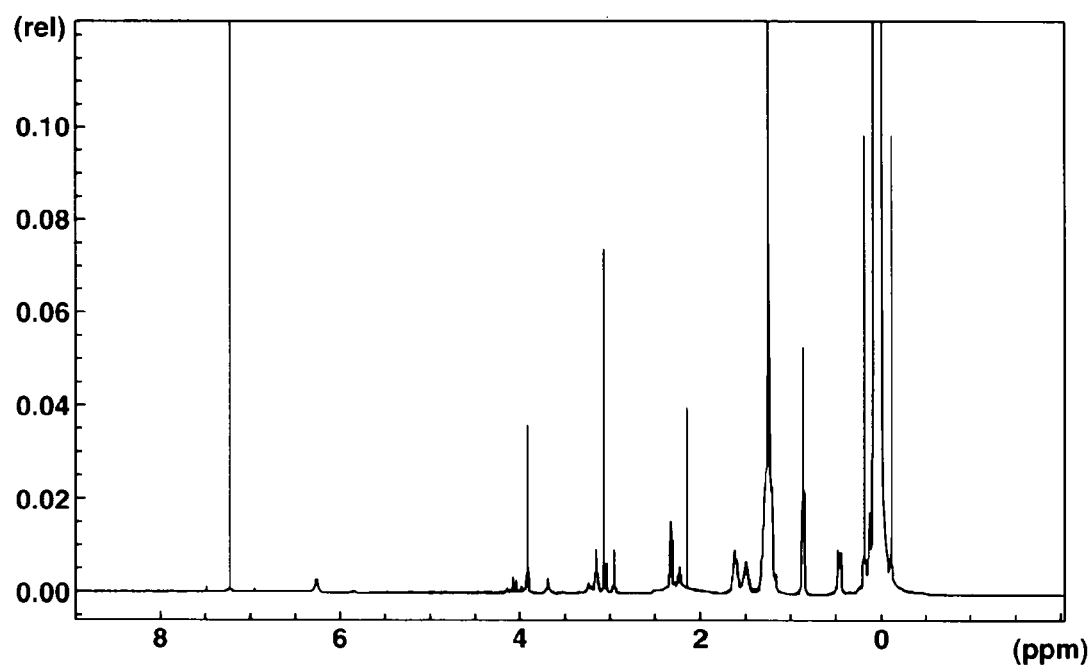
FIG. 5 is $^1$H-NMR chart of an amino acid-modified organopolysiloxane synthesized in Example 5.

A reactor was charged with 100 parts of a side chain aminopropylmethylsiloxane/dimethylsiloxane copolymer having an amine equivalent of 4,950 g/mol and a viscosity of 230 mm$^2$/sec at 25° C., 4 parts of titanium tetraethoxide, and 6.6 parts of N-lauroylsarcosine isopropyl. The contents were stirred at 100° C. for 8 hours. The reaction mixture was stripped at 120° C. in vacuum, obtaining 99 parts of a pale yellow, faintly turbid, viscous liquid in a yield of 93%. FIG. 5 shows the measurement results of $^1$H-NMR spectroscopy. In the $^1$H-NMR spectrum, the peak at 2.6 ppm assigned to the amine reactant extinguished and instead, the peak at approximately 3.1 ppm assigned to the amide bond formed was observed. In the IR spectrum, the absorption peak at 1,652 cm$^{-1}$ assigned to amide bond was observed, confirming that N-lauroylsarcosine isopropyl was bound to the aminopropyl-containing polysiloxane.

Comparative Example 1

A reactor was charged with 80 parts of tris(trimethylsiloxy) silylpropylamine and 30 parts of N,N-dimethylglycine ethyl. The contents were stirred at 80° C. for 4 hours. The reaction mixture was stripped at 100° C. in vacuum, obtaining a pale yellow clear liquid. On analysis of the liquid by $^1$H-NMR spectroscopy, the peak at approximately 3.1 ppm assigned to the amide bond was not observed. Also on analysis by IR spectroscopy, the absorption peak assigned to amide bond was not observed. These results confirmed no reaction between tris(trimethylsiloxy)silylpropylamine and N,N-dimethylglycine ethyl.

Comparative Example 2

A reactor was charged with 450 parts of a side chain aminopropylmethylsiloxane/dimethylsiloxane copolymer having an amine equivalent of 4,800 g/mol and a viscosity of 110 mm$^2$/sec at 25° C. and 11 parts of N-acetylglycine. The contents were stirred at 140° C. under a reduced pressure for 8 hours. As a result, 424 parts of a brown, faintly turbid, viscous liquid was obtained in a yield of 92%. The measurement results of the reaction mixture by $^1$H-NMR spectroscopy showed formation of salt (2.7 ppm) and amide (3.1 ppm) in a ratio of 3:7.

Examples 7 to 11 & Comparative Examples 3 to 7

Hair conditioners of the formulation shown in Table 1 were prepared by a standard technique. These hair conditioners were subjected to a sensory test as described below, with the results shown in Table 1.

Sensory Test

A panel of five members performed sensory evaluation while using a strand of Japanese female hair (20 g, 20 cm) which had been bleached with a commercial bleaching agent, and treating it as follows.

The hair strand was washed with 3 g of a standard shampoo of the following formulation.

Formulation of Standard Shampoo (pH 7.0)

| | |
|---|---|
| 25% Polyoxyethylene (2.5) lauryl ether sodium sulfate salt | 62.0 |
| Lauric acid diethanol amide | 2.3 |
| Disodium EDTA | 0.15 |
| Sodium benzoate | 0.5 |
| Sodium chloride | 0.8 |
| 75% Phosphoric acid | appropriate |
| Fragrance + methyl paraben | appropriate |
| Purified water | balance |
| Total | 100.0% |

To the hair strand, 2 g of the hair conditioner (Table 1) was applied so that all of the hair was contacted therewith. The hair strand was kept under flowing water at about 40° C. for 30 seconds whereupon the hair in the wet state was evaluated. Thereafter, the hair strand was towel dried and dried under a dryer, whereupon the hair in the dry state was evaluated. The sensory test evaluated smoothness, combing and softness in the wet state, and smoothness, combing, softness and luster in the dry state, which were rated according to the following criterion.

| Rating | Remarks |
|---|---|
| ⊚: | 4 or 5 members answered effective |
| ○: | 3 members answered effective |
| Δ: | 2 members answered effective |
| X: | 1 or 0 member answered effective |

TABLE 1

| | | Example | | | | | Comparative Example | | | | |
|---|---|---|---|---|---|---|---|---|---|---|---|
| | | 7 | 8 | 9 | 10 | 11 | 3 | 4 | 5 | 6 | 7 |
| 1 | Amino acid-modified organopolysiloxane synthesized in Example 2 | 2 | | | | | | | | | |
| 2 | Amino acid-modified organopolysiloxane synthesized in Example 4 | | 2 | | | | | | | | |
| 3 | Amino acid-modified organopolysiloxane synthesized in Example 5 | | | 2.5 | | | | | | | |
| 4 | Amino acid-modified organopolysiloxane synthesized in Example 2 | | | | 2 | | | | | | |
| 5 | Amino acid-modified organopolysiloxane synthesized in Example 2 | | | | | 2 | | | | | |
| 6 | Amino acid-modified organopolysiloxane synthesized in Example 2 | | | | | | 2 | | | | |
| 7 | Amino acid-modified organopolysiloxane synthesized in Example 4 | | | | | | | 2 | | | |
| 8 | Amino acid-modified organopolysiloxane synthesized in Comparative Example 2 | | | | | | | | 2 | | |
| 9 | Amino acid-modified organopolysiloxane synthesized in Comparative Example 2 | | | | | | | | | 2 | |
| 10 | Amino acid-modified organopolysiloxane synthesized in Comparative Example 2 | | | | | | | | | | 2 |
| 11 | Stearoxypropyldimethylamine | 1.8 | 1.8 | 1.8 | 1.8 | 1.8 | | 1.8 | 1.8 | 1.8 | 1.8 |

TABLE 1-continued

|  |  | Example | | | | | Comparative Example | | | | |
| --- | --- | --- | --- | --- | --- | --- | --- | --- | --- | --- | --- |
|  |  | 7 | 8 | 9 | 10 | 11 | 3 | 4 | 5 | 6 | 7 |
| 12 | Behenatotrimethylammonium chloride |  | 1.8 |  |  |  |  | 1.8 |  |  |  |
| 13 | Behenatopropyldimethylamine | 0.2 | 0.2 | 0.2 | 0.2 | 0.2 | 0.2 | 0.2 | 0.2 | 0.2 | 0.2 |
| 14 | Cetyl alcohol |  |  | 1 |  |  |  |  | 1 |  |  |
| 15 | Stearyl alcohol | 5.6 | 5.6 | 3.6 | 5.6 | 5.6 | 5.6 | 5.6 | 3.6 | 5.6 | 5.6 |
| 16 | Behenyl alcohol |  |  | 1 |  |  |  |  | 1 |  |  |
| 17 | Benzyl alcohol | 0.3 | 0.3 | 0.3 | 0.3 | 0.3 | 0.3 | 0.3 | 0.3 | 0.3 | 0.3 |
| 18 | Dipropylene glycol | 5 | 5 | 5 | 5 | 5 | 5 | 5 | 5 | 5 | 5 |
| 19 | Lactic acid | 1.35 | 1.35 | 1.35 |  | 1.35 | 1.35 | 1.35 | 1.35 |  | 1.35 |
| 20 | Glycolic acid | 0.2 | 0.2 | 0.2 |  |  | 0.2 | 0.2 | 0.2 |  |  |
| 21 | DL-malic acid | appropriate | appropriate | appropriate |  |  | appropriate | appropriate | appropriate |  |  |
| 22 | Fragrance |  |  |  |  |  | appropriate |  |  |  |  |
| 23 | Water |  |  |  |  |  | balance |  |  |  |  |
|  | Total (%) | 100.0 | 100.0 | 100.0 | 100.0 | 100.0 | 100.0 | 100.0 | 100.0 | 100.0 | 100.0 |
|  | pH | 3.2 | 3.2 | 3.2 | 9.3 | 5.8 | 3.2 | 3.2 | 3.2 | 9.3 | 5.8 |
| Evaluation | Smoothness in wet state | ○ | ⊚ | ⊚ | ⊚ | ⊚ | Δ | Δ | Δ | X | ○ |
|  | Combing in wet state | ⊚ | ○ | ⊚ | ⊚ | ⊚ | X | X | X | X | ○ |
|  | Softness in wet state | ○ | ⊚ | ⊚ | ⊚ | ○ | Δ | Δ | Δ | Δ | Δ |
|  | Smoothness in dry state | ⊚ | ⊚ | ⊚ | ⊚ | ⊚ | Δ | Δ | ○ | X | ○ |
|  | Combing in dry state | ⊚ | ○ | ⊚ | ⊚ | ⊚ | X | Δ | Δ | X | ○ |
|  | Softness in dry state | ⊚ | ⊚ | ⊚ | ○ | ⊚ | Δ | ○ | Δ | Δ | Δ |
|  | Luster in dry state | ⊚ | ○ | ○ | ⊚ | ○ | Δ | Δ | Δ | Δ | ○ |

Note that pH is measured at 25° C. after dilution with water to a 20-times amount by weight.

Example 12

O/W Hand Cream

|  | Ingredients | % by weight |
| --- | --- | --- |
| 1 | KP-545 | 10.0 |
| 2 | KP-561 | 8.0 |
| 3 | Cetanol | 1.0 |
| 4 | Glyceryl triisostearate | 5.0 |
| 5 | Stearic acid | 3.0 |
| 6 | Glyceryl monostearate | 1.5 |
| 7 | Amino acid-modified silicone in Example 6 | 1.0 |
| 8 | Sorbitan sesquioleate | 0.5 |
| 9 | Polyoxyethylene sorbitan monooleate | 1.0 |
| 10 | Sodium hydroxide (1% aqueous solution) | 10.0 |
| 11 | 1,3-Butylene glycol | 5.0 |
| 12 | Preservative | appropriate |
| 13 | Fragrance | appropriate |
| 14 | Purified water | balance |
|  | Total | 100.0% |

KP-545: acrylic silicone resin/decamethylcyclopentasiloxane solution (Shin-Etsu Chemical Co., Ltd.)
KP-561: stearyl-modified acrylic silicone resin (Shin-Etsu Chemical Co., Ltd.)

Preparation

The oil-in-water hand cream was prepared by the following steps.

Step A: Ingredients 1 to 9 were mixed and heat dissolved.

Step B: Ingredients 10, 11, 12 and 14 were mixed and heated.

Step C: B was added to A for emulsification. After cooling, ingredient 13 was added to the emulsion, obtaining the O/W hand cream.

The O/W hand cream thus prepared was humectant and non-greasy, and gave a moist pleasant feeling on use. The cream showed the moisturizing effect not only as applied, but also with the lapse of time. The moisturizing effect was not reduced even on exposure to water.

Example 13

A reactor was charged with 550 parts of a side chain aminopropylmethylsiloxane/dimethylsiloxane copolymer having an amine equivalent of 6,500 g/mol and a viscosity of 130 mm$^2$/sec at 25° C., 7 parts of titanium tetrabutoxide, and 17 parts of tyrosine ethyl. The contents were stirred at 100° C. for 8 hours. The reaction mixture was stripped at 120° C. in vacuum, obtaining 539 parts of a pale yellow, faintly turbid, viscous liquid in a yield of 95%. In the measurement results of $^1$H-NMR spectroscopy, the peak at 2.6 ppm assigned to the amine reactant extinguished and instead, the peak at approximately 3.1 ppm assigned to the amide bond formed was observed. In the measurement results of IR spectroscopy, the absorption peak at 1,650 cm$^{-1}$ assigned to amide bond was observed, confirming that tyrosine ethyl was bound to the aminopropyl-containing polysiloxane.

Example 14

A reactor was charged with 600 parts of a side chain aminopropylmethylsiloxane/dimethylsiloxane copolymer having an amine equivalent of 1,500 g/mol and a viscosity of 160 mm$^2$/sec at 25° C., 10 parts of titanium tetraethoxide, and 64 parts of 1-ethylproline ethyl. The contents were stirred at 100° C. for 8 hours. The reaction mixture was stripped at 120° C. in vacuum, obtaining 630 parts of a pale yellow, faintly turbid, viscous liquid in a yield of 95%. In the $^1$H-NMR spectrum, the peak at 2.6 ppm assigned to the amine reactant extinguished and instead, the peak at approximately 3.1 ppm assigned to the amide bond formed was observed. In the IR spectrum, the absorption peak at 1,660 cm$^{-1}$ assigned to amide bond was observed, confirming that 1-ethylproline ethyl was bound to the aminopropyl-containing polysiloxane.

In the following Examples, titanium oxide is commercially available under the trade name TTO-S-2 from Ishihara Sangyo Kaisha, Ltd., and zinc oxide is commercially available under the trade name ZnO350 from Sumitomo Osaka Cement Co., Ltd.

Synthesis Example 1

A dispersion (A) of surface treated titanium oxide was obtained by dissolving 8 g of the organopolysiloxane in Example 2 in 52 g of decamethylcyclopentasiloxane, adding 40 g of titanium oxide TTO-S-2 to the solution, and dispersing in a bead mill.

Synthesis Example 2

A dispersion (B) of surface treated zinc oxide was obtained by dissolving 6 g of the organopolysiloxane in Example 2 in 44 g of decamethylcyclopentasiloxane, adding 50 g of zinc oxide ZnO350 to the solution, and dispersing in a bead mill.

Synthesis Example 3

A dispersion (C) of surface treated titanium oxide was obtained by dissolving 6 g of the organopolysiloxane in Example 13 in 54 g of decamethylcyclopentasiloxane, adding 40 g of titanium oxide TTO-S-2 to the solution, and dispersing in a bead mill.

Synthesis Example 4

A dispersion (D) of surface treated zinc oxide was obtained by dissolving 8 g of the organopolysiloxane in Example 13 in 42 g of decamethylcyclopentasiloxane, adding 50 g of zinc oxide ZnO350 to the solution, and dispersing in a bead mill.

Synthesis Example 5

A dispersion (E) of surface treated titanium oxide was obtained by dissolving 6 g of the organopolysiloxane in Example 14 in a mixture of 10 g of decamethylcyclopentasiloxane and 44 g of isododecane, adding 40 g of titanium oxide TTO-S-2 to the solution, and dispersing in a bead mill.

Comparative Synthesis Example 1

A dispersion (F) of surface treated zinc oxide was obtained by dissolving 6 g of a polyether-modified silicone (KF-6017 by Shin-Etsu Chemical Co., Ltd.) in 44 g of decamethylcyclopentasiloxane, adding 50 g of zinc oxide ZnO350 to the solution, and dispersing in a bead mill.

Comparative Synthesis Example 2

A dispersion (G) of surface treated zinc oxide was obtained by dissolving 6 g of a polyglycerol-modified silicone (KF-6104 by Shin-Etsu Chemical Co., Ltd.) in 44 g of decamethylcyclopentasiloxane, adding 50 g of zinc oxide ZnO350 to the solution, and dispersing in a bead mill.

Comparative Synthesis Example 3

A dispersion (H) of surface treated titanium oxide was obtained by dissolving 6 g of a polyglycerol-modified silicone (KF-6104 by Shin-Etsu Chemical Co., Ltd.) in a mixture of 10 g of decamethylcyclopentasiloxane and 44 g of isododecane, adding 40 g of titanium oxide TTO-S-2 to the solution, and dispersing in a bead mill.

Synthesis Example 6

Surface treated titanium oxide (I) was obtained by dissolving 6 g of the organopolysiloxane in Example 2 in 2-propanol, adding 50 g of titanium oxide TTO-S-2 to the solution, dispersing the contents, and distilling off the solvent.

Synthesis Example 7

Surface treated zinc oxide (J) was obtained by dissolving 5 g of the organopolysiloxane in Example 13 in 2-propanol, adding 50 g of zinc oxide ZnO350 to the solution, dispersing the contents, and distilling off the solvent.

Comparative Synthesis Example 4

Surface treated titanium oxide (K) was obtained by dissolving 6 g of a polyether-modified silicone (KF-6017 by Shin-Etsu Chemical Co., Ltd.) in 2-propanol, adding 50 g of titanium oxide TTO-S-2 to the solution, dispersing the contents, and distilling off the solvent.

Comparative Synthesis Example 5

A surface treated zinc oxide (L) was obtained by dissolving 6 g of methylhydrogenpolysiloxane (KF-99 by Shin-Etsu Chemical Co., Ltd.) in 2-propanol, adding 50 g of zinc oxide ZnO350 to the solution, and drying at 100° C.

Examples 15 to 21 & Comparative Examples 8 to 11

Sunscreen compositions of the formulation (in parts by weight) shown in Table 2 were prepared and evaluated in quality.

TABLE 2

| | | Example | | | | | | | Comparative Example | | | |
|---|---|---|---|---|---|---|---|---|---|---|---|---|
| | | 15 | 16 | 17 | 18 | 19 | 20 | 21 | 8 | 9 | 10 | 11 |
| 1 | Titanium oxide dispersion (A) in Synthesis Example 1 | 55 | | | | | | | | | | |
| 2 | Zinc oxide dispersion (B) in Synthesis Example 2 | | 55 | | | | | | | | | |
| 3 | Titanium oxide dispersion (C) in Synthesis Example 3 | | | 55 | | | | | | | | |
| 4 | Zinc oxide dispersion (D) in Synthesis Example 4 | | | | 55 | | | | | | | |
| 5 | Titanium oxide dispersion (E) in Synthesis Example 5 | | | | | 55 | | | | | | |
| 6 | Titanium oxide dispersion (I) in Synthesis Example 6 | | | | | | 25 | | | | | |
| 7 | Zinc oxide dispersion (J) in Synthesis Example 7 | | | | | | | 25 | | | | |

TABLE 2-continued

| | | Example | | | | | | | Comparative Example | | | |
|---|---|---|---|---|---|---|---|---|---|---|---|---|
| | | 15 | 16 | 17 | 18 | 19 | 20 | 21 | 8 | 9 | 10 | 11 |
| 8 | Zinc oxide dispersion (F) in Comparative Synthesis Example 1 | | | | | | | | 55 | | | |
| 9 | Zinc oxide dispersion (G) in Comparative Synthesis Example 2 | | | | | | | | | 55 | | |
| 10 | Titanium oxide dispersion (H) in Comparative Synthesis Example 3 | | | | | | | | | | 55 | |
| 11 | Zinc oxide dispersion (L) in Comparative Synthesis Example 5 | | | | | | | | | | | 25 |
| 12 | RF-96 (6 cs) | 5 | 5 | 5 | 5 | 5 | 5 | 5 | 5 | 5 | 5 | 5 |
| 13 | KSG-21 | 5 | 5 | 5 | 5 | 5 | 5 | 5 | 5 | 5 | 5 | 5 |
| 14 | Isopropyl palmitate | 3 | 3 | 3 | 3 | 3 | 3 | 3 | 3 | 3 | 3 | 3 |
| 15 | KF-6017 | 1 | 1 | 1 | 1 | 1 | 1 | 1 | 1 | 1 | 1 | 1 |
| 16 | octylmethoxycinnamic acid | 6 | 6 | 6 | 6 | 6 | 6 | 6 | 6 | 6 | 6 | 6 |
| 17 | Sodium chloride | 0.5 | 0.5 | 0.5 | 0.5 | 0.5 | 0.5 | 0.5 | 0.5 | 0.5 | 0.5 | 0.5 |
| 18 | 1,3-Butanediol | 2 | 2 | 2 | 2 | 2 | 2 | 2 | 2 | 2 | 2 | 2 |
| 19 | Decamethylcyclopentasiloxane | | | | | | 25 | 25 | | | | 25 |
| 20 | Purified water | balance | | | | | | | | | | |
| 21 | Fragrance | appropriate | | | | | | | | | | |
| | Total (pbw) | 100.0 | 100.0 | 100.0 | 100.0 | 100.0 | 100.0 | 100.0 | 100.0 | 100.0 | 100.0 | 100.0 |
| Evaluation | Dispersion stability | ◉ | ◉ | ◉ | ◉ | ◉ | ◉ | ◉ | △ | ○ | △ | X |
| | Dryness | ◉ | ◉ | ◉ | ○ | ◉ | ◉ | ◉ | X | ○ | △ | △ |
| | Spreading | ◉ | ◉ | ◉ | ◉ | ◉ | ○ | ○ | △ | △ | △ | X |
| | Transparency of coating | ◉ | ◉ | ○ | ◉ | ◉ | ◉ | ◉ | ○ | △ | △ | △ |
| | Non-greasiness | ◉ | ○ | ◉ | ◉ | ◉ | ◉ | ◉ | X | ○ | △ | △ |
| | Long-lasting performance | ◉ | ◉ | ◉ | ○ | ◉ | ◉ | ◉ | X | △ | △ | X |
| | Sun-screen effect | ◉ | ○ | ◉ | ◉ | ○ | ○ | ○ | △ | △ | △ | △ |

Note that KF-96 is a trade name of dimethylpolysiloxane, KSG-21 is a trade name of silicone gel, and KF-6017 is a trade name of polyether-modified silicone, all available from Shin-Etsu Chemical Co., Ltd.

Sunscreens were prepared as follows. The sunscreens of Examples 15 to 19 and Comparative Examples 8 to 10 were prepared by the following steps.

Step A: Ingredients 12 to 15 were uniformly mixed.
Step B: Ingredients 17, 18 and 20 were uniformly mixed.
Step C: B was added to A for emulsification.
Step D: Ingredients 16, 21, and any one of ingredients 1 to 5 and 8 to 10 were added thereto.

The sunscreens of Examples 20 and 21 and Comparative Example 11 were prepared by the following steps.

Step A: Ingredients 12 to 15 were uniformly mixed, and ingredients 19, 21 and any one of ingredients 6, 7 and 11 were added thereto.
Step B: Ingredients 17, 18 and 20 were uniformly mixed.
Step C: B was added to A for emulsification, and ingredient 16 was added thereto.

The sunscreens of the formulation shown in Table 2 were evaluated in quality as follows.

1. Dispersion Stability of Powder

The sunscreen was held at room temperature for one month, after which it was observed whether particles agglomerated. Dispersion stability was judged according to the following criterion.

| Rating | Observation |
|---|---|
| ◉: | no particles agglomerated |
| ○: | some particles agglomerated |
| △: | particle agglomeration tendency |
| X: | apparent particle agglomeration |

2. Feeling on Use

A panel of 50 female members examined the sunscreens with respect to dryness, spreading, transparency of coating, stickiness to skin, long-lasting performance, and sun-screening effect, and rated on a 5-point scale according to the following criterion. For each item, an average point was computed and judged according to the following criterion.

| Point | Remarks |
|---|---|
| 5 | excellent |
| 4 | good |
| 3 | ordinary |
| 2 | fair |
| 1 | poor |

Judgment of Average Point

◉: average point a 4.5
○: 3.5 s average point<4.5
△: 2.5 s average point<3.5
X: 1.5 s average point<2.5

As is evident from the results in Table 2, the sunscreens of Examples 15 to 21 within the scope of the invention were good in dispersion because of no particle agglomeration. Their feeling on use was excellent in all items. By contrast, the sunscreens of Comparative Examples 8 to 11 having other silicones added were seen to contain agglomerated particles and to form a low transparent cosmetic coating, and their feeling on use was unsatisfactory.

Example 22

Foundation

| Ingredients | | % by weight |
|---|---|---|
| 1 | Decamethylcyclopentasiloxane | 8.3 |
| 2 | Dimethylpolysiloxane (6 mm²/s) | 5.0 |
| 3 | Polyether-modified silicone [1] | 2.0 |
| 4 | Octadecyldimethylbenzylammonium salt-modified montmorillonite | 4.0 |
| 5 | Powder dispersion [2] | 61.3 |
| 6 | Dipropylene glycol | 5.0 |
| 7 | Methyl p-hydroxybenzoate | 0.3 |
| 8 | 2-Amino-2-methyl-1,3-propane diol | 0.2 |
| 9 | Hydrochloric acid | 0.1 |
| 10 | Fragrance | appropriate |
| 11 | Purified water | balance |
| | Total | 100.0% |

[1] polyether-modified silicone commercially available under the trade name of KF-6017 from Shin-Etsu Chemical Co., Ltd.
[2] Powder dispersion obtained by dispersing the following ingredients in a bead mill.

| Titanium oxide | 15.0 |
|---|---|
| Talc | 9.0 |
| Mica | 9.0 |
| Red iron oxide | 2.4 |
| Yellow iron oxide | 1.0 |
| Black iron oxide | 0.3 |
| Silicone obtained in Example 13 | 10.0 |
| Decamethylpentasiloxane | 53.3 |
| Total | 100.0% |

The foundation was prepared by the following steps.

Step A: Ingredients 1 to 4 were heat mixed, and ingredient 5 was added thereto and uniformly mixed.

Step B: Ingredients 6 to 9 and 11 were heated and dissolved to form an aqueous solution at pH 9.0.

Step C: With stirring, B was slowly added to A for emulsification. After cooling, ingredient 10 was added to the emulsion, obtaining the foundation.

The foundation thus obtained had advantages including fine texture and ease of spreading, and gave a non-greasy, non-oily, moisturizing, fresh, and light feeling on use.

Example 23

Eye Shadow

| Ingredients | | % by weight |
|---|---|---|
| 1 | Decamethylcyclopentasiloxane | 15.0 |
| 2 | Dimethylpolysiloxane (6 mm²/s) | 10.0 |
| 3 | Polyether-modified silicone [1] | 2.0 |
| 4 | PEG (10) lauryl ether [2] | 0.5 |
| 5 | Chromium oxide treated with silicone compound in Example 13 | 6.2 |
| 6 | Ultramarine treated with silicone compound in Example 13 | 4.0 |
| 7 | Titanium-coated mica treated with silicone compound in Example 13 | 6.0 |
| 8 | Sodium chloride | 2.0 |
| 9 | Propylene glycol | 8.0 |
| 10 | Preservative | appropriate |
| 11 | Fragrance | appropriate |
| 12 | Purified water | balance |
| | Total | 100.0% |

[1] polyoxyalkylene/alkyl co-modified organopolysiloxane commercially available under the trade name of KF-6026 from Shin-Etsu Chemical Co., Ltd.
[2] PEG (10) means a connection of 10 polyethylene glycol units.

The eye shadow was prepared by the following steps.

Step A: Ingredients 1 to 4 were mixed, and ingredients 5 to 7 were added thereto and uniformly dispersed.

Step B: Ingredients 8, 9, 10 and 12 were uniformly dissolved.

Step C: With stirring, B was slowly added to A for emulsification. Finally, ingredient 11 was added to the emulsion, obtaining the eye shadow.

The dye shadow thus obtained had advantages including ease of spreading, and gave a non-oily, non-powdery, fresh, and light feeling on use. In addition, it has water resistance, water repellency and perspiration resistance and offered long-lasting performance, little make-up deterioration, and no changes with temperature and time, indicating high stability.

Example 24

Liquid Emulsified Foundation

| Ingredients | | % by weight |
|---|---|---|
| 1 | Dimethylpolysiloxane (6 mm²/s) | 5.0 |
| 2 | Squalane | 4.0 |
| 3 | Neopentylglycol dioctanoate | 3.0 |
| 4 | Myristic acid isostearic acid diglyceride | 2.0 |
| 5 | α-Monoisostearyl glyceryl ether | 1.0 |
| 6 | Polyether-modified silicone [1] | 1.0 |
| 7 | Aluminum distearate | 0.2 |
| 8 | Powder dispersion [2] | 26.2 |
| 9 | Magnesium sulfate | 0.7 |
| 10 | Glycerol | 3.0 |
| 11 | Preservative | appropriate |
| 12 | Fragrance | appropriate |
| 13 | Purified water | balance |
| | Total | 100.0% |

[1] polyoxyalkylene/alkyl co-modified organopolysiloxane commercially available under the trade name of KF-6026 from Shin-Etsu Chemical Co., Ltd.
[2] Powder dispersion obtained by dispersing the following ingredients in a bead mill.

| Titanium oxide | 20.0 |
|---|---|
| Sericite | 8.0 |
| Talc | 12.0 |
| Red iron oxide | 1.6 |
| Black iron oxide | 0.4 |
| Silicone obtained in Example 14 | 10.0 |
| Decamethylcyclopentasiloxane | 48.0 |
| Total | 100.0% |

The foundation was prepared by the following steps.

Step A: Ingredients 1 to 7 and 10 were heat mixed, and ingredient 8 was added thereto and uniformly mixed.

Step B: Ingredients 9, 10, 11 and 12 were heated and dissolved.

Step C: With stirring, B was slowly added to A for emulsification. After cooling, ingredient 12 was added to the emulsion, obtaining the liquid emulsified foundation.

The liquid emulsified foundation thus obtained had advantages including low viscosity, fine texture and ease of spreading, and gave a non-greasy, non-oily, moisturizing, fresh, and light feeling on use. It also offered long-lasting performance, and no changes with temperature and time, indicating high stability.

Example 25

Eye Liner

| | Ingredients | % by weight |
|---|---|---|
| 1 | Decamethylcyclopentasiloxane | 22.0 |
| 2 | Dimethylpolysiloxane (6 mm²/s) | 5.0 |
| 3 | Black iron oxide treated with silicone compound in Example 14 | 20.0 |
| 4 | Vitamin E acetate | 0.2 |
| 5 | Jojoba oil | 2.0 |
| 6 | Bentonite | 3.0 |
| 7 | Polyether-modified silicone [1] | 2.0 |
| 8 | Ethanol | 10.0 |
| 9 | 1,3-butylene glycol | 10.0 |
| 10 | Preservative | appropriate |
| 11 | Fragrance | appropriate |
| 12 | Purified water | balance |
| | Total | 100.0% |

[1] polyether-modified silicone commercially available under the trade name of KF-6017 from Shin-Etsu Chemical Co., Ltd.

The eye liner was prepared by the following steps.

Step A: Ingredients 1, 2, 4 to 7 were mixed, and ingredient 3 was added thereto, mixed and dispersed until uniform.

Step B: Ingredients 8, 9, 10 and 12 were mixed.

Step C: With stirring, B was slowly added to A for emulsification. After cooling, ingredient 11 was added to the emulsion, obtaining the eye liner.

The eye liner thus obtained had advantages including ease of spreading, easy drawing, and gave a refreshing, light, and non-greasy feeling on use. It underwent no changes with temperature and time, and offered good applicability and stability as well as water resistance, perspiration resistance and long-lasting performance.

Example 26

Sun Cut Cream

| | Ingredients | % by weight |
|---|---|---|
| 1 | Decamethylcyclopentasiloxane | 17.5 |
| 2 | KP-545 [1] | 12.0 |
| 3 | Glyceryl triisooctanoate | 5.0 |
| 4 | Octyl p-methoxycinnamate | 6.0 |
| 5 | KSG-21 [2] | 5.0 |
| 6 | Polyether-modified silicone [3] | 1.0 |
| 7 | Zinc oxide composition (D) in Synthesis Example 4 | 20.0 |
| 8 | Sodium chloride | 0.5 |
| 9 | 1,3-butylene glycol | 2.0 |
| 10 | Preservative | appropriate |
| 11 | Fragrance | appropriate |
| 12 | Purified water | balance |
| | Total | 100.0% |

[1] KP-545: trade name of acrylic silicone by Shin-Etsu Chemical Co., Ltd.
[2] KSG-21: trade name of silicone gel by Shin-Etsu Chemical Co., Ltd.
[3] polyoxyalkylene/alkyl co-modified organopolysiloxane commercially available under the trade name of KF-6026 from Shin-Etsu Chemical Co., Ltd.

The sun cut cream was prepared by the following steps.

Step A: Ingredient 2 was added to a part of ingredient 1 and uniformly mixed, ingredient 7 was added thereto, and the contents were dispersed in a bead mill.

Step B: The remainder of ingredient 1 and ingredients 3 to 6 were uniformly mixed.

Step C: Ingredients 8, 9, 10 and 12 were mixed and dissolved.

Step D: With stirring, C was added to B for emulsification. A and ingredient 11 were added to the emulsion, obtaining the sun cut cream.

The sun cut cream thus obtained had advantages including non-greasy, light spreading, good adherence, good setting, lustrous finish, and was stable against temperature changes and time, ensuring long-lasting performance.

Japanese Patent Application No. 2010-231329 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An amino acid-modified organopolysiloxane having a backbone comprising organosiloxane segments, wherein an organic group having the general formula (1) is bonded to at least one silicon atom in the organosiloxane segments,

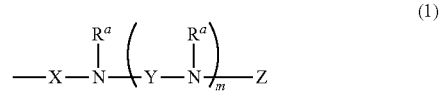

(1)

wherein X and Y are each independently a divalent $C_1$-$C_{10}$ hydrocarbon group, m is an integer of 0 to 4, $R^a$ is hydrogen or a monovalent $C_1$-$C_4$ hydrocarbon group, and Z is an organic group having the general formula (2):

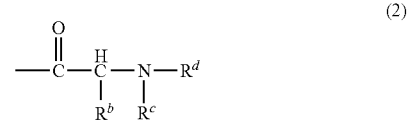

(2)

wherein $R^b$ is a side chain of an amino acid, le is hydrogen or $C_1$-$C_6$ alkyl, and $R^d$ is hydrogen or $C_1$-$C_6$ alkyl.

2. The amino acid-modified organopolysiloxane of claim 1, having the general formula (3):

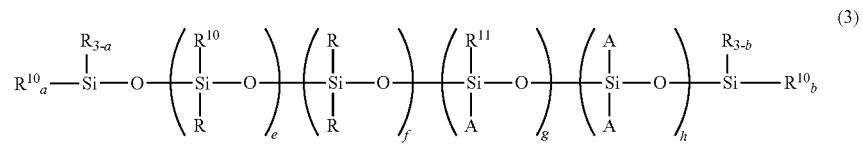

(3)

wherein R is each independently selected from the group consisting of hydrogen, hydroxyl, $C_1$-$C_3$ alkoxy, $C_1$-$C_{30}$ alkyl, $C_1$-$C_{30}$ fluoroalkyl, $C_6$-$C_{30}$ aryl, and $C_7$-$C_{30}$ aralkyl, $R^{10}$ is an organic group having formula (1), $R^{11}$ is an organic group selected from the group consisting of R and $R^{10}$, A is a segment having the general formula (4):

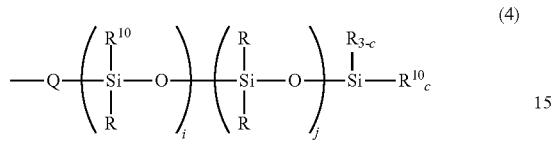

(4)

wherein R and $R^{10}$ are as defined above, and Q is an oxygen atom or a divalent $C_1$-$C_3$ hydrocarbon group, the subscripts a, b, and c are each independently an integer of 0 to 3, e is an integer of 0 to 100, f is an integer of 0 to 5,000, g is 0 or 1, h is 0 or 1, i is an integer of 0 to 100, j is an integer of 0 to 5,000, satisfying 1≤a+b+c+e+g+i when $R^{11}$ is $R^{10}$, and 1≤a+b+c+e+i when $R^{11}$ is R.

3. The amino acid-modified organopolysiloxane of claim 1, wherein the amino acid is selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, sarcosine, γ-aminobutyric acid, ornithine, creatine, opine, cystine, hydroxyproline, hydroxylysine, thyroxine, O-phosphoserine, and valine.

4. A method for preparing the amino acid-modified organopolysiloxane of claim 1, said method comprising reacting an amino-modified organopolysiloxane with an amino acid or amino acid derivative ester in the presence of an organometallic catalyst, said amino-modified organopolysiloxane having a backbone comprising organosiloxane segments wherein an amino group having the general formula (5):

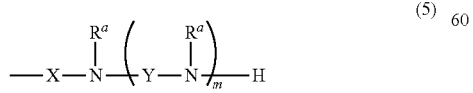

(5)

wherein X, Y, m, and $R^a$ are as defined for the general formula (1) is bonded to at least one silicon atom in the organosiloxane segments, said amino acid or amino acid derivative ester being an amino acid or amino acid derivative whose carboxyl group has been esterified and having the general formula (6):

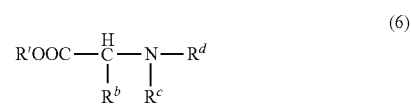

(6)

wherein R' is a monovalent $C_1$-$C_7$ hydrocarbon group, and $R^b$, $R^c$, and $R^d$ are as defined for the general formula (2).

5. The method of claim 4 wherein said amino-modified organopolysiloxane has the general formula (7):

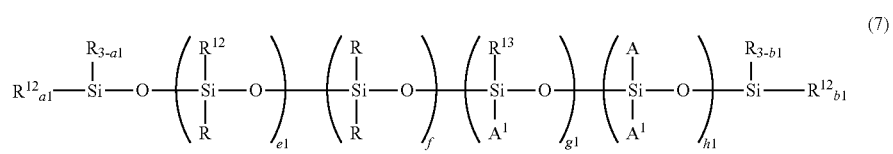

(7)

wherein R is each independently selected from the group consisting of hydrogen, hydroxyl, $C_1$-$C_3$ alkoxy, $C_1$-$C_{30}$ alkyl, $C_1$-$C_{30}$ fluoroalkyl, $C_6$-$C_{30}$ aryl, and $C_7$-$C_{30}$ aralkyl, $R^{12}$ is an organic group having formula (5), $R^{13}$ is an organic group selected from the group consisting of R and $R^{12}$, $A^1$ is a segment having the general formula (8):

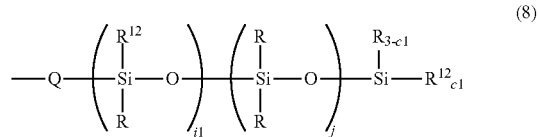

(8)

wherein R and $R^{12}$ are as defined above, and Q is an oxygen atom or a divalent $C_1$-$C_3$ hydrocarbon group, the subscripts a1, b1, and c1 are each independently an integer of 0 to 3, e1 is an integer of 0 to 100, f is an integer of 0 to 5,000, g1 is 0 or 1, h1 is 0 or 1, i1 is an integer of 0 to 100, j is an integer of 0 to 5,000, satisfying 1≤a1+b1+c1+e1+g1+i1 when $R^{13}$ is $R^{12}$, and 1≤a1+b1+c1+e1+i1 when $R^{13}$ is R, and said amino acid-modified organopolysiloxane has the general formula (3):

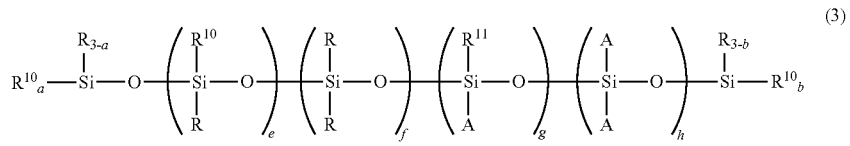
(3)

wherein R is as defined above, $R^{10}$ is an organic group having formula (1),
$R^{11}$ is an organic group selected from the group consisting of R and $R^{10}$,
A is a segment having the general formula (4):

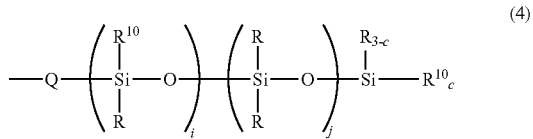
(4)

wherein R, $R^{10}$ and Q are as defined above, and a, b, c, e, f, g, h, i, and j are as defined above.

6. The method of claim 4, wherein said amino acid or amino acid derivative ester has an ester group selected from the group consisting of methyl, ethyl, propyl, butyl, heptyl, hexyl, and benzyl.

7. The method of claim 4, wherein said amino acid ester has an amino acid residue which is selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, sarcosine, γ-aminobutyric acid, ornithine, creatine, opine, cystine, hydroxyproline, hydroxylysine, thyroxine, O-phosphoserine, and valine residues.

8. The method of claim 4, wherein said amino acid derivative ester has an amino acid derivative residue which is selected from the group consisting of N-acylamino acid, N-alkylamino acid, and N,N-dialkylamino acid residues.

9. The method of claim 8, wherein the N-acyl is acetyl, propanoyl, butanoyl, pentanoyl, hexanoyl, benzoyl, lauroyl, or stearoyl.

10. The method of claim 4, wherein the reaction is conducted in an organic solvent.

11. The method of claim 4, wherein the reaction is conducted at a temperature of 25° C. to 120° C.

12. The method of claim 4, wherein the organometallic catalyst comprises a metal atom selected from the elements of Group 4 and Group 13 in the Periodic Table.

13. The method of claim 12, wherein the organometallic catalyst is a tetraalkoxytitanium, tetraalkoxyzirconium or trialkoxyaluminum.

14. A cosmetic composition comprising the amino acid-modified organopolysiloxane of claim 1.

15. A cosmetic composition comprising a powder treated with the amino acid-modified organopolysiloxane of claim 1.

* * * * *